(12) United States Patent
Ullrich, Jr. et al.

(10) Patent No.: US 8,591,590 B2
(45) Date of Patent: *Nov. 26, 2013

(54) SPINAL IMPLANT HAVING A TRANSVERSE APERTURE

(75) Inventors: Peter F. Ullrich, Jr., Neenah, WI (US); Chad J. Patterson, Port Washington, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/571,714

(22) Filed: Aug. 10, 2012

(65) Prior Publication Data

US 2012/0316653 A1  Dec. 13, 2012

Related U.S. Application Data

(63) Continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.
*A61F 2/44* (2006.01)

(52) U.S. Cl.
USPC .................................. 623/17.16; 623/17.11

(58) Field of Classification Search
USPC ............................................ 623/17.11–17.16
See application file for complete search history.

(56) References Cited

U.S. PATENT DOCUMENTS

| | | |
|---|---|---|
| 4,314,876 A | 2/1982 | Kremer et al. |
| 4,904,261 A | 2/1990 | Dove et al. |
| 5,015,247 A | 5/1991 | Michelson |
| 5,071,437 A | 12/1991 | Steffee |
| 5,192,327 A * | 3/1993 | Brantigan .................. 623/17.11 |
| 5,258,098 A | 11/1993 | Wagner et al. |
| 5,306,308 A | 4/1994 | Gross et al. |
| 5,306,309 A | 4/1994 | Wagner et al. |
| 5,425,772 A | 6/1995 | Brantigan |
| 5,443,514 A | 8/1995 | Steffee |

(Continued)

FOREIGN PATENT DOCUMENTS

| | | |
|---|---|---|
| EP | 0599419 | 6/1994 |
| EP | 0916323 | 5/1999 |

(Continued)

OTHER PUBLICATIONS

Wennerberg, A., et al., "Effects of titanium surface topography on bone integration: a systematic review", Clin. Oral Impl. Res., 20 (Suppl. 4), 2009, pp. 172-184.

(Continued)

*Primary Examiner* — Eduardo C Robert
*Assistant Examiner* — Julianna N Harvey
(74) *Attorney, Agent, or Firm* — Stradley Ronon Stevens & Young, LLP

(57) ABSTRACT

An interbody spinal implant including a body having a top surface, a bottom surface, opposing lateral sides, opposing anterior and posterior portions, and optionally a substantially hollow center. The implant includes at least one transverse aperture on one or more of the posterior portion, the anterior portion, and at least one of the opposing lateral sides, and if the substantially hollow center is present, one or more of the transverse apertures may be in communication with the hollow center. The transverse aperture may comprise a notch.

24 Claims, 34 Drawing Sheets

(56) References Cited

U.S. PATENT DOCUMENTS

| | | | | |
|---|---|---|---|---|
| 5,456,723 | A | 10/1995 | Steinemann et al. | |
| 5,507,815 | A | 4/1996 | Wagner et al. | |
| 5,571,188 | A | 11/1996 | Ellingsen et al. | |
| 5,603,338 | A | 2/1997 | Beaty | |
| 5,609,635 | A | 3/1997 | Michelson | |
| 5,702,449 | A | 12/1997 | McKay | |
| 5,702,451 | A * | 12/1997 | Biedermann et al. | 623/17.16 |
| 5,755,798 | A * | 5/1998 | Papavero et al. | 623/17.16 |
| 5,766,252 | A * | 6/1998 | Henry et al. | 623/17.16 |
| 5,776,199 | A | 7/1998 | Michelson | |
| 5,860,973 | A | 1/1999 | Michelson | |
| 5,863,201 | A | 1/1999 | Lazzara et al. | |
| 5,865,845 | A | 2/1999 | Thalgott | |
| 5,876,453 | A | 3/1999 | Beaty | |
| 5,885,079 | A | 3/1999 | Niznick | |
| 5,888,224 | A | 3/1999 | Beckers et al. | |
| 5,922,029 | A | 7/1999 | Wagner et al. | |
| 5,968,098 | A | 10/1999 | Winslow | |
| 5,984,922 | A | 11/1999 | McKay | |
| 6,033,582 | A | 3/2000 | Lee et al. | |
| 6,039,762 | A | 3/2000 | McKay | |
| 6,059,829 | A | 5/2000 | Schlapfer et al. | |
| 6,080,158 | A | 6/2000 | Lin | |
| 6,086,613 | A | 7/2000 | Camino et al. | |
| 6,096,107 | A | 8/2000 | Caracostas et al. | |
| 6,123,705 | A | 9/2000 | Michelson | |
| 6,143,032 | A | 11/2000 | Schafer et al. | |
| 6,176,882 | B1 | 1/2001 | Biedermann et al. | |
| 6,183,255 | B1 | 2/2001 | Oshida | |
| 6,193,757 | B1 | 2/2001 | Foley et al. | |
| 6,193,762 | B1 | 2/2001 | Wagner et al. | |
| 6,241,770 | B1 | 6/2001 | Michelson | |
| 6,241,771 | B1 | 6/2001 | Gresser et al. | |
| 6,245,108 | B1 | 6/2001 | Biscup | |
| 6,296,664 | B1 | 10/2001 | Middleton | |
| 6,302,914 | B1 * | 10/2001 | Michelson | 623/17.16 |
| 6,342,074 | B1 | 1/2002 | Simpson | |
| 6,344,057 | B1 | 2/2002 | Rabbe et al. | |
| 6,350,283 | B1 | 2/2002 | Michelson | |
| 6,375,681 | B1 | 4/2002 | Truscott | |
| 6,387,130 | B1 | 5/2002 | Stone et al. | |
| 6,395,031 | B1 | 5/2002 | Foley et al. | |
| 6,423,095 | B1 | 7/2002 | Van Hoeck et al. | |
| 6,432,140 | B1 | 8/2002 | Lin | |
| 6,436,102 | B1 | 8/2002 | Ralph et al. | |
| 6,447,544 | B1 | 9/2002 | Michelson | |
| 6,458,159 | B1 | 10/2002 | Thalgott | |
| 6,478,823 | B1 | 11/2002 | Michelson | |
| 6,482,233 | B1 | 11/2002 | Aebi et al. | |
| 6,485,517 | B1 | 11/2002 | Michelson | |
| 6,491,723 | B1 | 12/2002 | Beaty | |
| 6,520,993 | B2 | 2/2003 | James et al. | |
| 6,558,424 | B2 | 5/2003 | Thalgott | |
| 6,569,201 | B2 | 5/2003 | Moumene et al. | |
| 6,579,318 | B2 | 6/2003 | Varga et al. | |
| 6,592,624 | B1 | 7/2003 | Fraser et al. | |
| 6,599,322 | B1 | 7/2003 | Amrich et al. | |
| 6,610,089 | B1 | 8/2003 | Liu et al. | |
| 6,620,332 | B2 | 9/2003 | Amrich | |
| 6,635,086 | B2 | 10/2003 | Lin | |
| 6,652,765 | B1 | 11/2003 | Beaty | |
| 6,676,703 | B2 | 1/2004 | Biscup | |
| 6,702,855 | B1 | 3/2004 | Steinemann et al. | |
| 6,719,794 | B2 | 4/2004 | Gerber et al. | |
| 6,726,720 | B2 | 4/2004 | Ross et al. | |
| 6,730,127 | B2 | 5/2004 | Michelson | |
| 6,740,118 | B2 | 5/2004 | Eisermann et al. | |
| 6,743,231 | B1 | 6/2004 | Gray et al. | |
| 6,758,849 | B1 | 7/2004 | Michelson | |
| 6,833,006 | B2 | 12/2004 | Foley et al. | |
| 6,890,355 | B2 | 5/2005 | Michelson | |
| 6,902,581 | B2 | 6/2005 | Walkenhorst et al. | |
| 6,911,249 | B2 | 6/2005 | Wagner et al. | |
| 6,923,810 | B1 | 8/2005 | Michelson | |
| 6,964,687 | B1 * | 11/2005 | Bernard et al. | 623/17.16 |
| 6,974,480 | B2 * | 12/2005 | Messerli et al. | 623/17.16 |
| 6,981,975 | B2 | 1/2006 | Michelson | |
| 7,018,418 | B2 | 3/2006 | Amrich et al. | |
| 7,041,137 | B2 | 5/2006 | Fulton et al. | |
| 7,044,972 | B2 | 5/2006 | Mathys, Jr. et al. | |
| 7,048,870 | B1 | 5/2006 | Ellingsen et al. | |
| 7,060,073 | B2 | 6/2006 | Frey et al. | |
| 7,066,961 | B2 | 6/2006 | Michelson | |
| 7,077,864 | B2 | 7/2006 | Byrd, III et al. | |
| 7,087,085 | B2 | 8/2006 | Steinemann et al. | |
| 7,112,224 | B2 | 9/2006 | Liu et al. | |
| 7,128,760 | B2 | 10/2006 | Michelson | |
| 7,137,997 | B2 | 11/2006 | Paul | |
| 7,144,428 | B2 | 12/2006 | Anitua | |
| 7,166,129 | B2 | 1/2007 | Michelson | |
| 7,169,183 | B2 | 1/2007 | Liu et al. | |
| D539,934 | S | 4/2007 | Blain | |
| 7,201,775 | B2 | 4/2007 | Gorensek et al. | |
| D541,940 | S | 5/2007 | Blain | |
| 7,220,280 | B2 | 5/2007 | Kast et al. | |
| 7,223,289 | B2 | 5/2007 | Trieu et al. | |
| 7,226,480 | B2 | 6/2007 | Thalgott | |
| 7,238,186 | B2 | 7/2007 | Zdeblick et al. | |
| 7,244,275 | B2 | 7/2007 | Michelson | |
| 7,250,060 | B2 | 7/2007 | Trieu | |
| 7,255,698 | B2 | 8/2007 | Michelson | |
| 7,288,093 | B2 | 10/2007 | Michelson | |
| 7,311,734 | B2 | 12/2007 | Van Hoeck et al. | |
| D564,095 | S | 3/2008 | Blain | |
| 7,347,873 | B2 | 3/2008 | Paul et al. | |
| D566,276 | S | 4/2008 | Blain | |
| 7,368,065 | B2 | 5/2008 | Yang et al. | |
| 7,410,501 | B2 | 8/2008 | Michelson | |
| 7,501,073 | B2 | 3/2009 | Wen et al. | |
| 7,503,933 | B2 | 3/2009 | Michelson | |
| 7,517,363 | B2 | 4/2009 | Rogers et al. | |
| D599,019 | S | 8/2009 | Pimenta et al. | |
| 7,569,074 | B2 | 8/2009 | Eisermann et al. | |
| 7,608,107 | B2 | 10/2009 | Michelson | |
| 7,615,078 | B2 | 11/2009 | White et al. | |
| 7,655,042 | B2 | 2/2010 | Foley et al. | |
| 7,662,186 | B2 | 2/2010 | Bagga et al. | |
| 7,662,190 | B2 | 2/2010 | Steinemann et al. | |
| 7,744,612 | B2 | 6/2010 | Blain | |
| 7,846,183 | B2 | 12/2010 | Blain | |
| 7,901,462 | B2 | 3/2011 | Yang et al. | |
| 7,998,172 | B2 | 8/2011 | Blain | |
| 8,062,304 | B2 | 11/2011 | Blain et al. | |
| 8,100,955 | B2 | 1/2012 | Blain et al. | |
| 8,142,355 | B2 | 3/2012 | Blain et al. | |
| 8,172,854 | B2 | 5/2012 | Blain et al. | |
| 8,262,737 | B2 | 9/2012 | Bagga et al. | |
| 2001/0014826 | A1 | 8/2001 | Biedermann et al. | |
| 2001/0016777 | A1 * | 8/2001 | Biscup | 623/17.16 |
| 2001/0039454 | A1 | 11/2001 | Ricci et al. | |
| 2001/0047208 | A1 | 11/2001 | Michelson | |
| 2002/0049497 | A1 * | 4/2002 | Mason | 623/17.11 |
| 2002/0087212 | A1 * | 7/2002 | James et al. | 623/17.11 |
| 2002/0099443 | A1 | 7/2002 | Messerli et al. | |
| 2002/0128716 | A1 | 9/2002 | Cohen et al. | |
| 2002/0138142 | A1 | 9/2002 | Castro et al. | |
| 2002/0161443 | A1 | 10/2002 | Michelson | |
| 2002/0173854 | A1 | 11/2002 | Amrich | |
| 2002/0188294 | A1 | 12/2002 | Couture et al. | |
| 2003/0004576 | A1 * | 1/2003 | Thalgott | 623/17.16 |
| 2003/0014116 | A1 | 1/2003 | Ralph et al. | |
| 2003/0023306 | A1 * | 1/2003 | Liu et al. | 623/17.11 |
| 2003/0083668 | A1 | 5/2003 | Rogers et al. | |
| 2003/0105527 | A1 | 6/2003 | Bresina | |
| 2003/0109928 | A1 | 6/2003 | Pasquet et al. | |
| 2003/0125739 | A1 | 7/2003 | Bagga et al. | |
| 2003/0153975 | A1 | 8/2003 | Byrd, III et al. | |
| 2003/0176925 | A1 | 9/2003 | Paponneau | |
| 2003/0181980 | A1 | 9/2003 | Berry et al. | |
| 2003/0181981 | A1 | 9/2003 | Lemaire | |
| 2003/0187506 | A1 | 10/2003 | Ross et al. | |
| 2003/0191531 | A1 * | 10/2003 | Berry et al. | 623/17.11 |
| 2004/0117019 | A1 | 6/2004 | Trieu et al. | |
| 2004/0117020 | A1 | 6/2004 | Frey et al. | |

(56) References Cited

U.S. PATENT DOCUMENTS

| | | |
|---|---|---|
| 2004/0122518 A1 | 6/2004 | Rhoda |
| 2004/0127993 A1* | 7/2004 | Kast et al. ............... 623/17.16 |
| 2004/0153154 A1 | 8/2004 | Dinkelacker |
| 2004/0153160 A1 | 8/2004 | Carrasco |
| 2004/0162616 A1* | 8/2004 | Simonton et al. ......... 623/17.11 |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1* | 2/2005 | Webb et al. .............. 623/17.11 |
| 2005/0038512 A1 | 2/2005 | Michelson |
| 2005/0060034 A1 | 3/2005 | Berry et al. |
| 2005/0071005 A1* | 3/2005 | Carli et al. ............... 623/17.11 |
| 2005/0075734 A1 | 4/2005 | Fulton et al. |
| 2005/0085913 A1 | 4/2005 | Fraser et al. |
| 2005/0101960 A1* | 5/2005 | Fiere et al. ................... 606/72 |
| 2005/0131416 A1 | 6/2005 | Jansen et al. |
| 2005/0143822 A1* | 6/2005 | Paul ........................ 623/17.16 |
| 2005/0147942 A1 | 7/2005 | Hall |
| 2005/0159814 A1 | 7/2005 | Karahalios |
| 2005/0251257 A1 | 11/2005 | Mitchell et al. |
| 2005/0261771 A1* | 11/2005 | Paul et al. ................. 623/17.11 |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0123990 A1* | 5/2007 | Sharifi-Mehr ............ 623/17.16 |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0270951 A1 | 11/2007 | Davis et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0154378 A1 | 6/2008 | Pelo |
| 2008/0195209 A1 | 8/2008 | Garcia et al. |
| 2008/0221689 A1 | 9/2008 | Chaput et al. |
| 2008/0249622 A1 | 10/2008 | Gray |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2009/0005784 A1 | 1/2009 | Blain et al. |
| 2009/0014243 A1 | 1/2009 | Whigham |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2011/0040301 A1 | 2/2011 | Blain et al. |
| 2011/0082503 A1 | 4/2011 | Blain |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1 | 11/2011 | Ullrich, Jr. et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wenzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1 | 7/2012 | Bertele et al. |
| 2012/0232664 A1 | 9/2012 | Ullrich, Jr. et al. |
| 2012/0239150 A1 | 9/2012 | Ullrich, Jr. et al. |
| 2012/0239151 A1 | 9/2012 | Ullrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |

FOREIGN PATENT DOCUMENTS

| | | |
|---|---|---|
| EP | 1449544 | 8/2004 |
| EP | 2 386 274 A1 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004041131 | 5/2004 |
| WO | 1449544 | 8/2004 |
| WO | 2006081843 | 8/2006 |
| WO | 2006116306 | 11/2006 |
| WO | 2006119088 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |

OTHER PUBLICATIONS

Pending U.S. Appl. No. 13/286,813 of Chad J. Patterson, et al. filed Nov. 1, 2011.
Pending U.S. Appl. No. 13/826,304 of Peter F. Ullrich, Jr., et al. filed Mar. 14, 2013.
Pending U.S. Appl. No. 13/713,417 of Chad J. Patterson, et al. filed Dec. 13, 2012.
Pending U.S. Appl. No. 13/784,144 of Peter F. Ullrich, Jr., et al. filed Mar. 4, 2013.
Astra Tech Dental, "Nanolevel topographic modifications on the OsseoSpeed surface", http://shop.dentsplyimplants.us, Mar. 8, 2001.
Astra Tech Dental, "OsseoSpeed—more bone more rapidly", http://shop.dentsplyimplants.us, May 2011.

(56) References Cited

OTHER PUBLICATIONS

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growth of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011, for EP 06 75 9086.

Supplementary Partial European Search Report issued Aug. 19, 2011, for EP 06 75 9086.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

\* cited by examiner

FIG. 16A
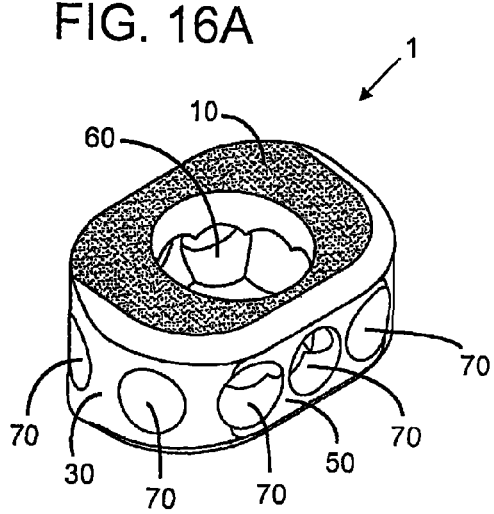
FIG. 16B
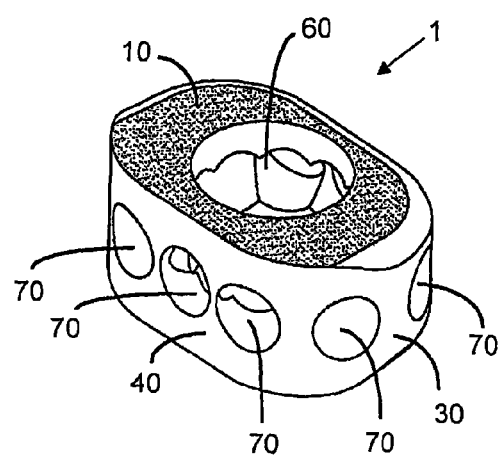
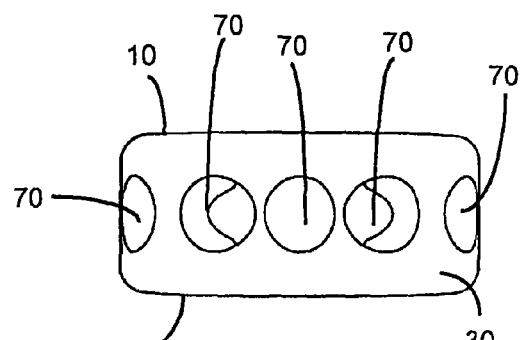
FIG. 16C
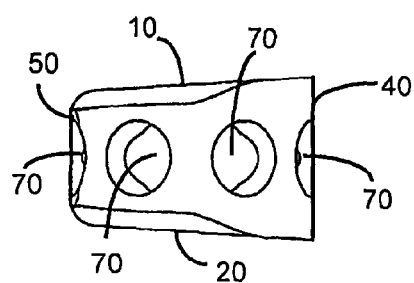
FIG. 16D

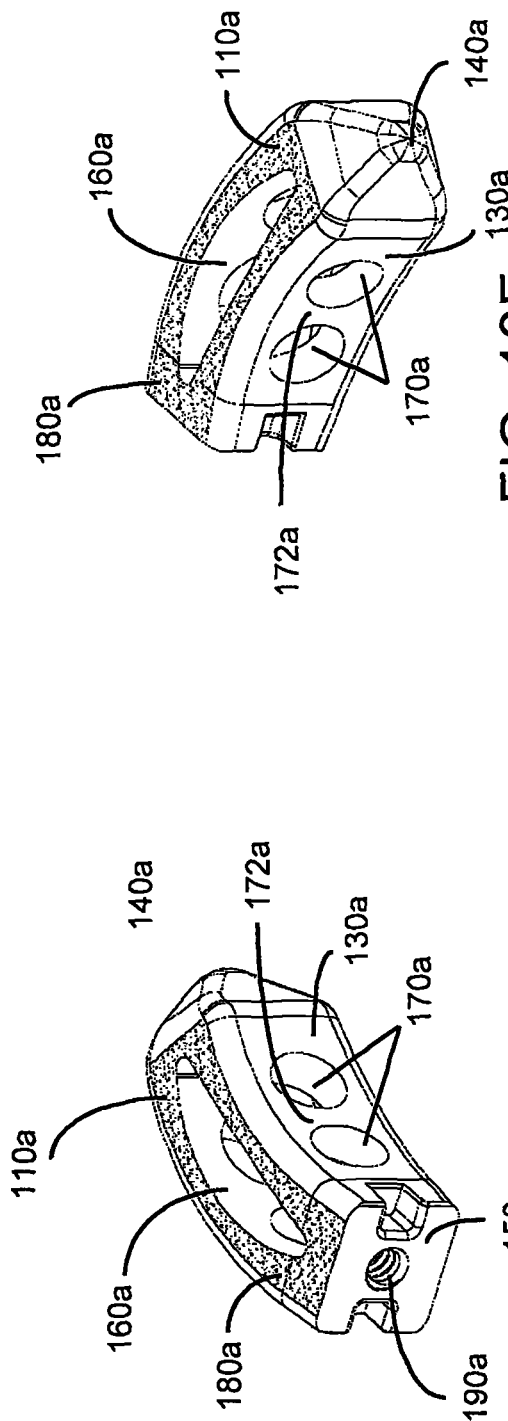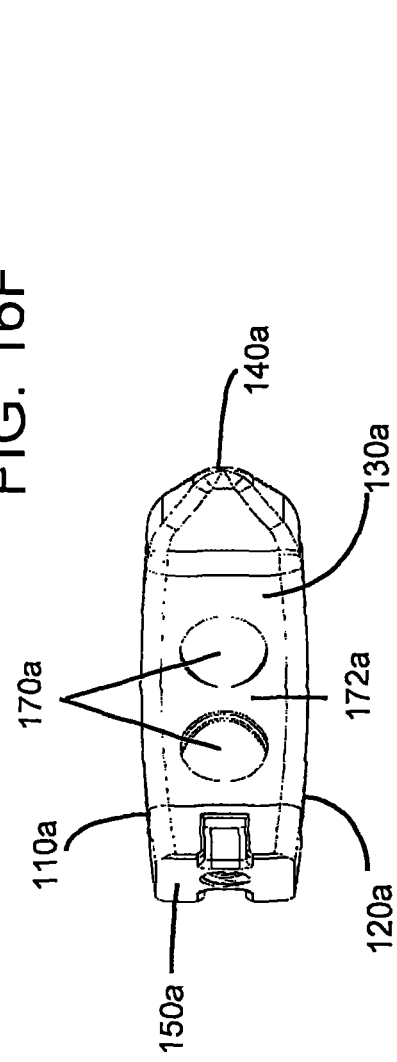
FIG. 16E  FIG. 16F  FIG. 16G

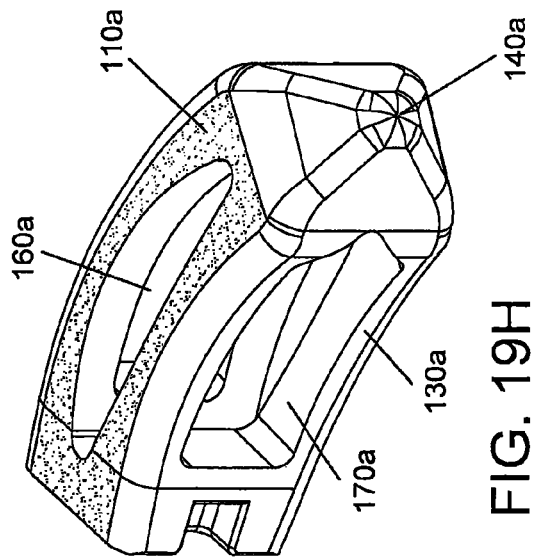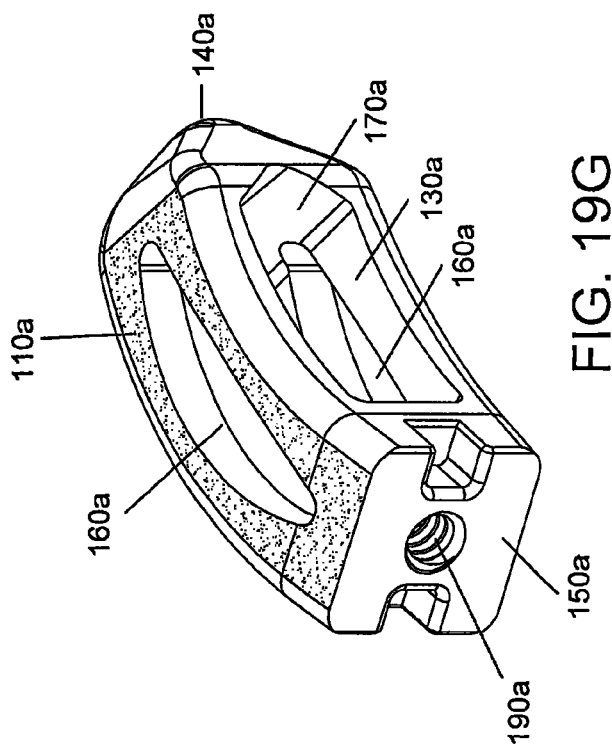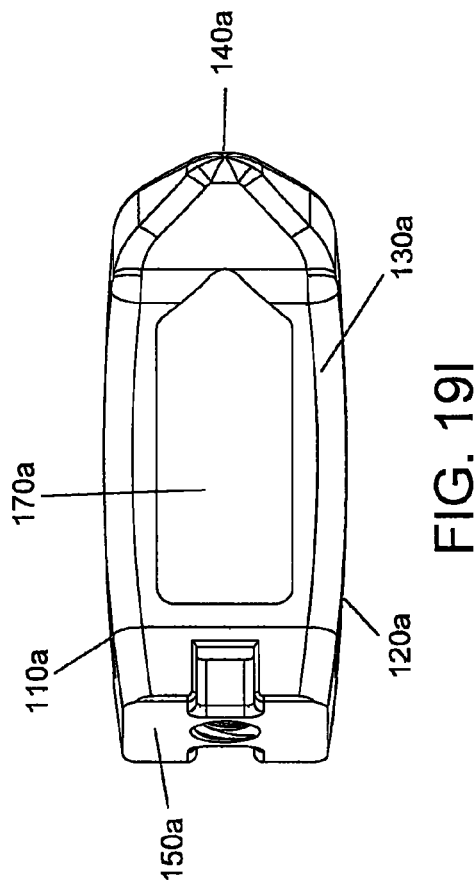

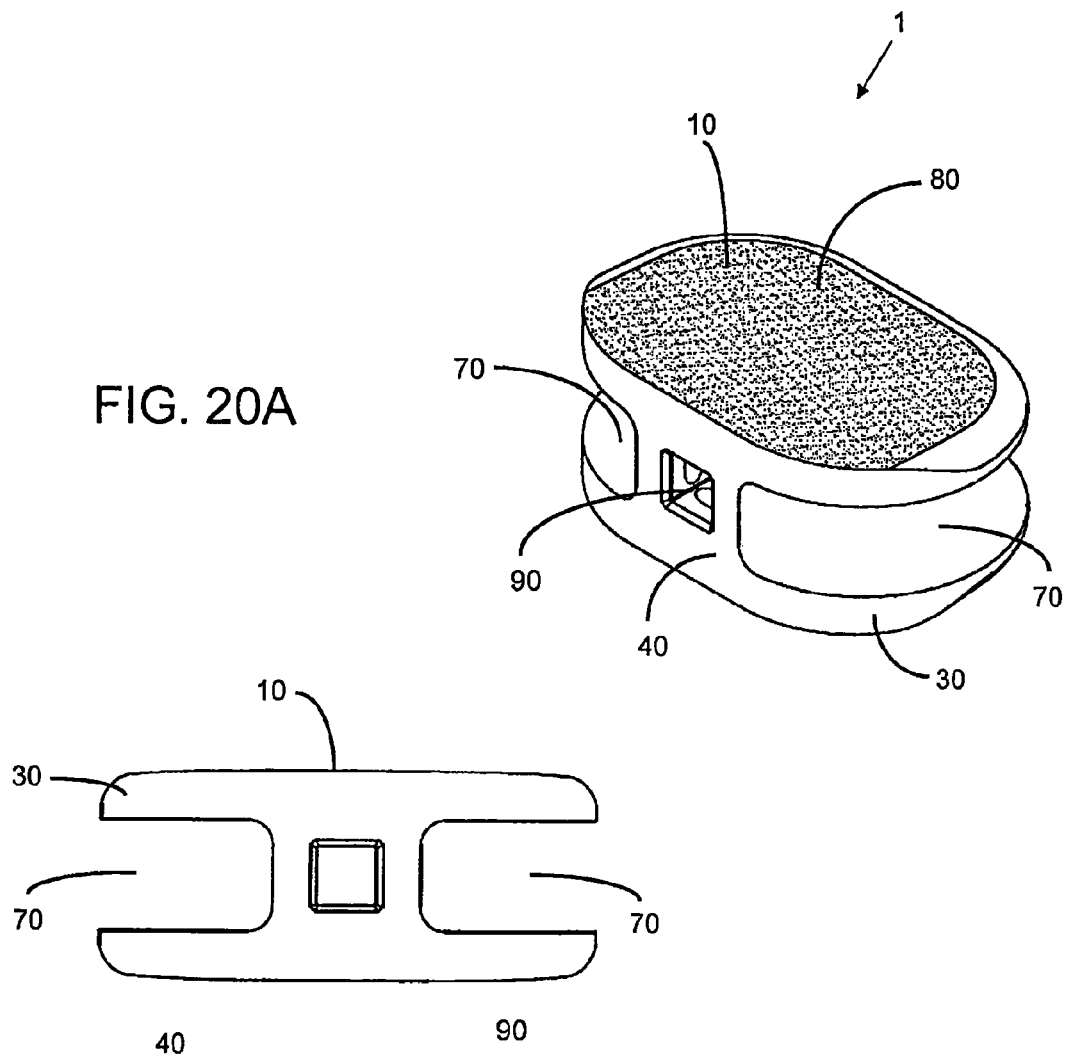
FIG. 20A
FIG. 20B
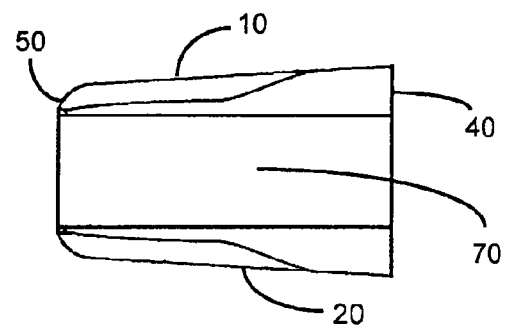
FIG. 20C

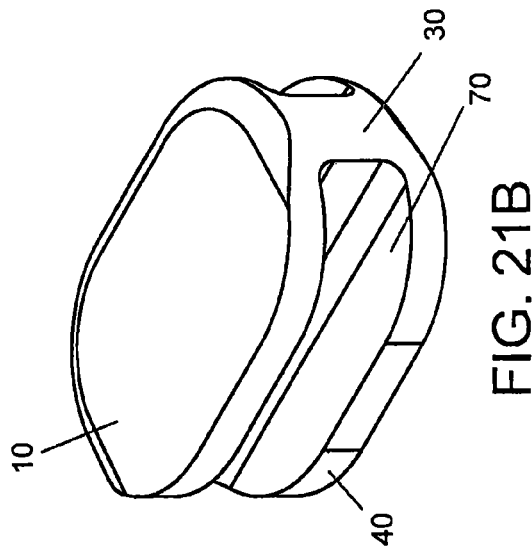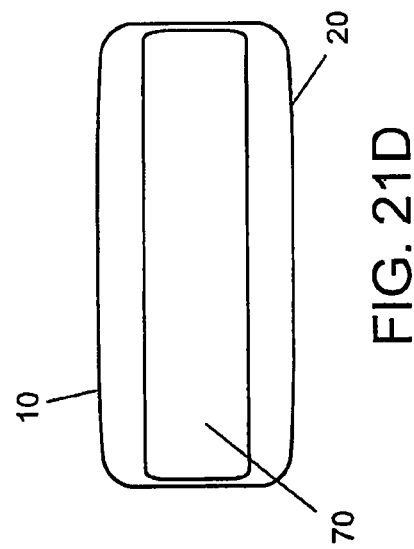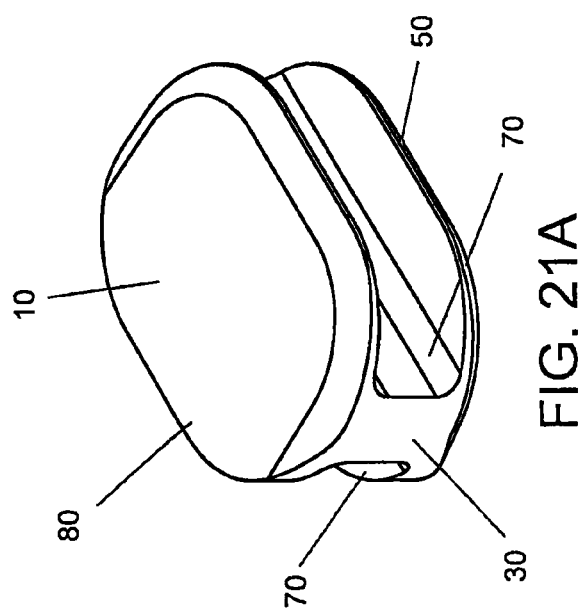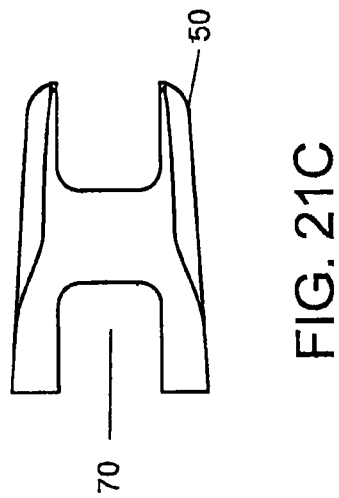

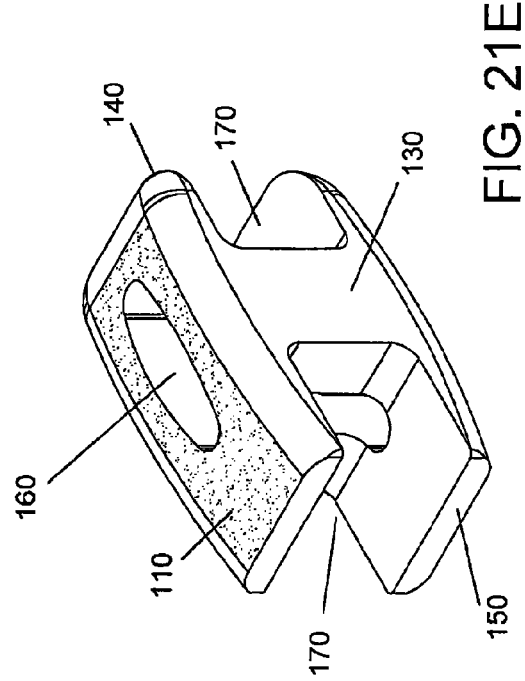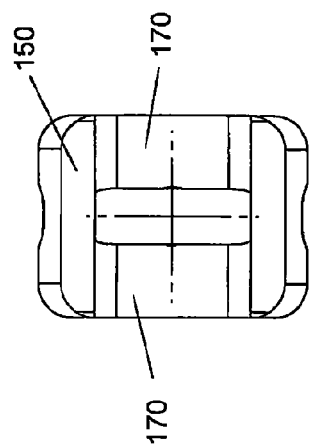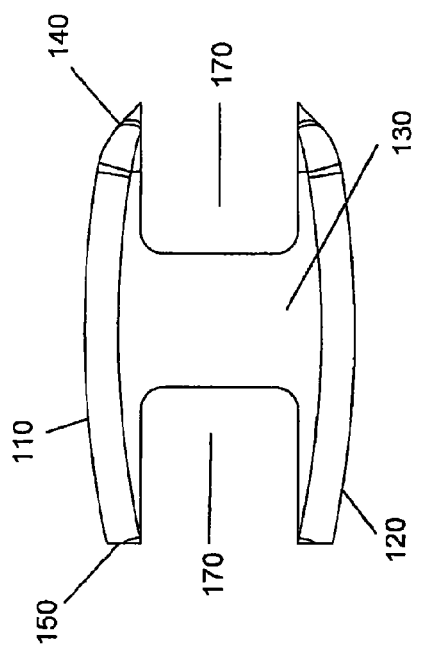

US 8,591,590 B2

SPINAL IMPLANT HAVING A TRANSVERSE APERTURE

CROSS REFERENCE TO RELATED APPLICATIONS

This application is a continuation-in-part of U.S. patent application Ser. No. 12/151,198, filed on May 5, 2008, and pending, which is a continuation-in-part of U.S. patent application Ser. No. 11/123,359, filed on May 6, 2005, and issued as U.S. Pat. No. 7,662,186. The contents of both prior applications are incorporated by reference in this document, in their entirety and for all purposes.

FIELD OF THE INVENTION

The invention relates generally to interbody spinal implants and methods of using such implants and, more particularly, to an implant including a transverse aperture on one or more of its anterior, posterior or lateral portions.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Several interbody implant systems have been introduced to facilitate interbody fusion. Traditional threaded implants involve at least two cylindrical bodies, each typically packed with bone graft material, surgically placed on opposite sides of the mid-sagittal plane through pre-tapped holes within the intervertebral disc space. This location is not the preferable seating position for an implant system, however, because only a relatively small portion of the vertebral endplate is contacted by these cylindrical implants. Accordingly, these implant bodies will likely contact the softer cancellous bone rather than the stronger cortical bone, or apophyseal rim, of the vertebral endplate. The seating of these threaded cylindrical implants may also compromise biomechanical integrity by reducing the area in which to distribute mechanical forces, thus increasing the apparent stress experienced by both the implant and vertebrae. Still further, a substantial risk of implant subsidence (defined as sinking or settling) into the softer cancellous bone of the vertebral body may arise from such improper seating.

In contrast, open ring-shaped cage implant systems are generally shaped to mimic the anatomical contour of the vertebral body. Traditional ring-shaped cages are generally comprised of allograft bone material, however, harvested from the human femur. Such allograft bone material restricts the usable size and shape of the resultant implant. For example, many of these femoral ring-shaped cages generally have a medial-lateral width of less than 25 mm. Therefore, these cages may not be of a sufficient size to contact the strong cortical bone, or apophyseal rim, of the vertebral endplate. These size-limited implant systems may also poorly accommodate related instrumentation such as drivers, reamers, distractors, and the like. For example, these implant systems may lack sufficient structural integrity to withstand repeated impact and may fracture during implantation. Still further, other traditional non-allograft ring-shaped cage systems may be size-limited due to varied and complex supplemental implant instrumentation which may obstruct the disc space while requiring greater exposure of the operating space. These supplemental implant instrumentation systems also generally increase the instrument load upon the surgeon.

The surgical procedure corresponding to an implant system should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Nevertheless, traditional implantation practices often do not preserve critical bone structures such as vertebral endplates during the surgical procedure. In some cases, the implant devices themselves necessitate removal of bone and were not designed or implanted with the intent to preserve critical bone structures during or after implantation.

In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

SUMMARY OF THE INVENTION

The invention is directed to interbody spinal implants and to methods of using such implants. The implants can be inserted, using methods of the invention, from a variety of vantages, including anterior, antero-lateral, and lateral implantation. The spinal implant is preferably adapted to be inserted into a prepared disc space via a procedure which does not destroy the vertebral end-plates, or contacts the vertebral end-plates only peripherally, allowing the intact vertebral end-plates to deflect like a diaphragm under axial compressive loads generated due to physiologic activities and pressurize the bone graft material disposed inside the spinal implant.

The invention features an interbody spinal implant comprising a body having a top surface, a bottom surface, opposing lateral sides, and opposing anterior and posterior portions. The body may optionally comprise a substantially hollow center. In preferred aspects, the implant comprises at least one transverse aperture on one or more of the posterior portion, the anterior portion, and at least one of the opposing lateral sides of the body. If the body comprises a substantially hollow center, the transverse aperture may extend into this substantially hollow center. The implant may also comprise a roughened surface topography adapted to grip bone and inhibit migration of the implant on at least a portion of the top surface, the bottom surface, or both the top and bottom surfaces.

In some aspects, the implant optionally comprises a single vertical aperture extending from the top surface to the bottom surface and defining a transverse rim on the top surface and on the bottom surface having an anterior section, a posterior section, opposing lateral sections, and a maximum width at its center ranging from about 40% to about 80% of the distance between the opposing lateral sections. Generally speaking, embodiments including a single vertical aperture will also include a substantially hollow center, although in some aspects, the implant may include a single vertical aperture but not a substantially hollow center. The single vertical aperture may be in communication with the substantially hollow center. And, in some aspects, the single vertical aperture and the transverse aperture extend into the substantially hollow center.

In some aspects, the implant comprises at least one transverse aperture on the posterior portion, and at least one transverse aperture on the anterior portion. The anterior portion transverse aperture, the posterior potion transverse aperture, or both may extend into the substantially hollow center, or may extend into the single vertical aperture if this single vertical aperture is present. The anterior portion transverse aperture, the posterior potion transverse aperture, or both may comprise a notch. In aspects where the transverse aperture comprises a notch, the implant preferably does not comprise a substantially hollow center, and also preferably does not comprise a single vertical aperture, although the implant may comprise either or both of the substantially hollow center and the single vertical aperture when the transverse aperture comprises a notch.

In some aspects, the implant comprises at least one transverse aperture on each of the opposing lateral sides. In some such aspects, the implant does not have a transverse aperture on the anterior portion, but the anterior portion may comprise an opening for engaging a delivery device. In some such aspects, the implant does not have a transverse aperture on the posterior portion, but the posterior portion may comprise an opening for engaging a delivery device. The implant may comprise at least one transverse aperture on the posterior portion, and this posterior portion transverse aperture may extend into the substantially hollow center. Each lateral side transverse aperture may extend into the substantially hollow center, or may extend into the single vertical aperture if this single vertical aperture is present. Each lateral side transverse aperture may comprise a notch. In aspects where the transverse aperture comprises a notch, the implant preferably does not comprise a substantially hollow center, and also preferably does not comprise a single vertical aperture, although the implant may comprise either or both of the substantially hollow center and the single vertical aperture when the transverse aperture comprises a notch.

In some aspects, the implant comprises at least one transverse aperture on the posterior portion, on the anterior portion, and on each of the opposing lateral sides. The at least one transverse aperture on the posterior portion, on the anterior portion, and on each of the opposing lateral sides may extend into the substantially hollow center. Each transverse aperture on the posterior portion, on the anterior portion, and on each of the opposing lateral sides may comprise a notch, and in such embodiments, the implant preferably does not comprise a substantially hollow center and preferably does not comprise a single vertical aperture. The implant comprises a plurality of transverse apertures on the posterior portion, on the anterior portion, and on each of the opposing lateral sides, and each one of the plurality of transverse apertures may extend into the substantially hollow center.

The transverse aperture, optionally the substantially hollow portion of the body, and optionally the single vertical aperture may contain a bone graft material adapted to facilitate the formation of a solid fusion column within the spine. The bone graft material may be cancellous autograft bone, allograft bone, demineralized bone matrix (DBM), porous synthetic bone graft substitute, bone morphogenic protein (BMP), or a combination thereof.

The implant body may be fabricated from a metal. A preferred metal is titanium. The implant body may be fabricated from a non-metallic material, non-limiting examples of which include polyetherether-ketone, hedrocel, ultra-high molecular weight polyethylene, and combinations thereof. The implant body may be fabricated from both a metal and a non-metallic material, including a composite thereof. For example, a composite may be formed, in part, of titanium and, in part, of polyetherether-ketone, hedrocel, ultra-high molecular weight polyethylene, or combinations thereof.

In some embodiments, the implant further comprises an integration plate joined to either or both of the top surface and the bottom surface of the body. Each integration plate comprises a top surface, a bottom surface, opposing lateral sides, opposing anterior and posterior portions, and optionally, a single vertical aperture extending from the top surface to the bottom surface that aligns with the single vertical aperture of the body if the body single vertical aperture is present.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 16A shows a perspective of an oval-shaped implant having multiple transverse apertures on the posterior face and a lateral face;

FIG. 16B shows a perspective of an oval-shaped implant having multiple transverse apertures on the posterior face and a lateral face;

FIG. 16C shows an anterior perspective of an oval-shaped implant having multiple transverse apertures;

FIG. 16D shows a side perspective of an oval-shaped implant having multiple transverse apertures;

FIG. 16E shows a perspective of a curved implant having multiple transverse apertures on the lateral sides, but not the posterior portion;

FIG. 16F shows a perspective of a curved implant having multiple transverse apertures on the lateral sides, but not the anterior portion;

FIG. 16G shows a side perspective of a curved implant having multiple transverse apertures on the lateral sides, but not the anterior or posterior portions;

FIG. 19G shows a perspective of a curved implant having a tall vertical height, with a transverse aperture on each of the lateral sides;

FIG. 19H shows an anterior perspective of a curved implant with a tall height and a transverse aperture on each of the lateral sides;

FIG. 19I shows a side perspective of a curved implant with a tall height and a transverse aperture on a lateral side;

FIG. 20A shows a perspective of an oval-shaped implant having no single vertical aperture and a transverse aperture configured as a notch into each of the lateral sides of the implant;

FIG. 20B shows an anterior perspective of an oval-shaped implant having no single vertical aperture and a transverse aperture configured as a notch into each of the lateral sides of the implant;

FIG. 20C shows a side perspective of an oval-shaped implant having no single vertical aperture and a transverse aperture configured as a notch into a lateral side of the implant;

FIG. 21A shows a perspective of an oval-shaped implant having no single vertical aperture, and having a transverse aperture configured as a notch into each of the anterior and posterior sides of the implant, extending from one lateral side to the other;

FIG. 21B shows a perspective of an oval-shaped implant having no single vertical aperture, and having a transverse aperture configured as a notch into each of the anterior and posterior portions of the implant, extending from one lateral side to the other;

FIG. 21C shows a side perspective of an oval-shaped implant having a transverse aperture configured as a notch into each of the anterior and posterior portions of the implant;

FIG. 21D shows an anterior perspective of an oval-shaped implant having a transverse aperture configured as a notch into each of the anterior and posterior portions of the implant;

FIG. 21E shows a perspective of a posterior implant having a single vertical aperture and having a transverse aperture configured as a notch into each of the anterior and posterior portions of the implant;

FIG. 21F shows a side perspective of a posterior implant having a transverse aperture configured as a notch into each of the anterior and posterior portions of the implant;

FIG. 21G shows a posterior perspective of a posterior implant having a transverse aperture configured as a notch into the posterior portion of the implant;

DETAILED DESCRIPTION OF THE INVENTION

Certain embodiments of the invention may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the invention, allow for improved visualization of implant seating and fusion assessment. Interbody spinal implants, as now taught, may also facilitate osteointegration with the surrounding living bone.

Anterior interbody spinal implants in accordance with certain aspects of the invention can be preferably made of a durable material such as stainless steel, stainless steel alloy, titanium, or titanium alloy, but can also be made of other durable materials such as, but not limited to, polymeric, ceramic, and composite materials. For example, certain embodiments of the invention may be comprised of a biocompatible, polymeric matrix reinforced with bioactive fillers, fibers, or both. Certain embodiments of the invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments of the invention due to their acceptable, and desirable, strength and biocompatibility. In this manner, certain embodiments of the present interbody spinal implant may have improved structural integrity and may better resist fracture during implantation by impact. Interbody spinal implants, as now taught, may therefore be used as a distractor during implantation.

Figure 1A:
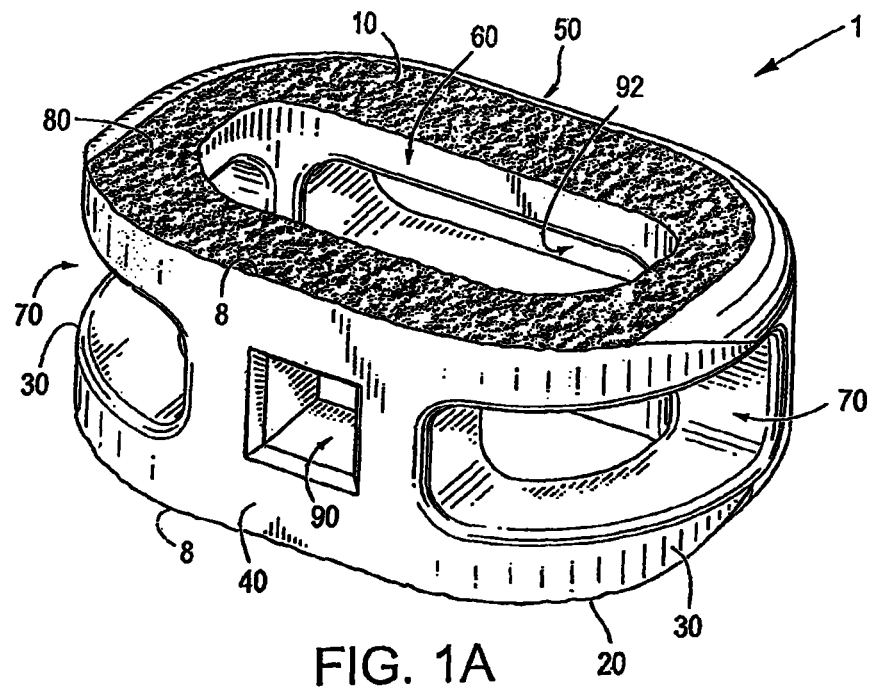
FIG. 1A shows a perspective view of an embodiment of the interbody spinal implant having a generally oval shape and roughened surface topography on the top surface.
Figure 1B:
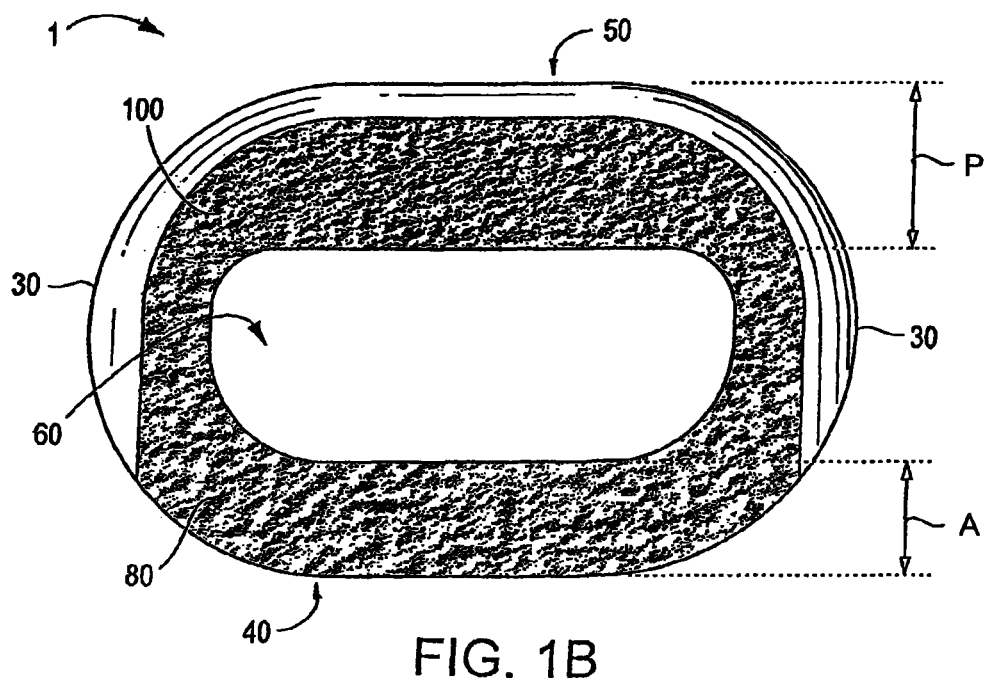
FIG. 1B shows a top view of the first embodiment of the interbody spinal implant illustrated in FIG. 1A.

Referring now to the drawing, in which like reference numbers refer to like elements throughout the various figures that comprise the drawing, FIG. 1 shows a perspective view of a first embodiment of the interbody spinal implant 1 especially well adapted for use in an ALIF procedure.

The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. The roughened topography 80, however, is distinct from the teeth provided on the surfaces of some conventional devices.

It is generally believed that the surface of an implant determines its ultimate ability to integrate into the surrounding living bone. Without being limited to any particular theory or mechanism of action, it is believed that the cumulative effects of at least implant composition, implant surface energy, and implant surface roughness play a major role in the biological response to, and osteointegration of, an implant device. Thus, implant fixation may depend, at least in part, on the attachment and proliferation of osteoblasts and like-functioning cells upon the implant surface.

It is believed that cells attach more readily to relatively rough surfaces rather than smooth surfaces. In this manner, a surface may be bioactive due to its ability to facilitate cellular attachment and osteointegration. The surface roughened topography 80 may better promote the osteointegration of the implant 1. The surface roughened topography 80 may also better grip the vertebral endplate surfaces and inhibit implant migration of the implant 1 upon placement and seating in a patient.

Accordingly, the implant 1 further includes the roughened topography 80 on at least a portion of its top 10 and bottom 20 surfaces for gripping adjacent bone and inhibiting migration of the implant 1. FIG. 1 shows roughened topography 80 on an embodiment of the implant 1.

The roughened topography 80 may be obtained through a variety of techniques including, without limitation, chemical etching, shot peening, plasma etching, laser etching, or abrasive blasting (such as sand or grit blasting). In at least one embodiment, the interbody spinal implant 1 may be comprised of titanium, or a titanium alloy, having the surface roughened topography 80. The surfaces of the implant 1 are preferably bioactive.

In a preferred embodiment of the invention, the roughened topography 80 is obtained via the repetitive masking and chemical or electrochemical milling processes described in U.S. Pat. No. 5,258,098; No. 5,507,815; No. 5,922,029; and No. 6,193,762. Each of these patents is incorporated in this document by reference. Where the invention employs chemical etching, the surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features.

By way of example, an etchant mixture of nitric acid ($HNO_3$) and hydrofluoric (HF) acid may be repeatedly applied to a titanium surface to produce an average etch depth of about 0.53 mm. Interbody spinal implants 1, in accordance with some preferred embodiments of the invention, may be comprised of titanium, or a titanium alloy, having an average surface roughness of about 100 μm. Surface roughness may be measured using a laser profilometer or other standard instrumentation.

In another example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles) and this surface can be bioactive, for example, by inducing or supporting bone formation by cellular reactions.

The implant 1 may be shaped to reduce the risk of subsidence, and improve stability, by maximizing contact with the apophyseal rim of vertebral endplates. Embodiments may be provided in a variety of anatomical footprints having a medial-lateral width ranging from about 32 mm to about 44 mm. An interbody spinal implant 1 generally does not require extensive supplemental or obstructive implant instrumentation to maintain the prepared disc space during implantation. Thus, the interbody spinal implant 1 and associated implantation methods allow for larger-sized implants as compared with other size-limited interbody spinal implants known in the art. This advantage allows for greater medial-lateral width and correspondingly greater contact with the apophyseal rim. The implant 1 may also include an anti-expulsion edge 8 as described in more detail below.

In some embodiments, for example, as illustrated in FIG. 1, the implant 1 has an opening 90 in the anterior portion 40. In one embodiment the posterior portion 50 has a similarly shaped opening 90. In some aspects, only the anterior portion 40 has the opening 90 while the posterior portion 50 has an alternative opening 92 (which may have a size and shape different from the opening 90).

The opening 90 has a number of functions. One function is to facilitate manipulation of the implant 1 by the caretaker. Thus, the caretaker may insert a surgical tool into the opening 90 and, through the engagement between the surgical tool and the opening 90, manipulate the implant 1. The opening 90 may be threaded to enhance the engagement.

Certain embodiments of the invention are particularly suited for use during interbody spinal implant procedures (or vertebral body replacement procedures) and may act as a final distractor during implantation, thus minimizing the instrument load upon the surgeon. For example, in such a surgical procedure, the spine may first be exposed via an anterior approach and the center of the disc space identified. The disc space is then initially prepared for implant insertion by removing vertebral cartilage. Soft tissue and residual cartilage may then also be removed from the vertebral endplates.

Vertebral distraction may be performed using trials of various-sized embodiments of the interbody spinal implant 1. The determinatively sized interbody implant 1 may then be inserted in the prepared disc space for final placement. The distraction procedure and final insertion may also be performed under fluoroscopic guidance. The substantially hollow area within the implant body may optionally be filled, at least partially, with bone fusion-enabling materials such as, without limitation, cancellous autograft bone, allograft bone, DBM, porous synthetic bone graft substitute, BMP, or combinations of those materials. Such bone fusion-enabling material may be delivered to the interior of the interbody spinal implant 1 using a delivery device mated with the opening 90 in the anterior portion 40 of the implant 1. The interbody spinal implant 1 may be generally larger than those currently known in the art, and therefore have a correspondingly larger hollow area which may deliver larger volumes of fusion-enabling bone graft material. The bone graft material may be delivered such that it fills the full volume, or less than the full volume, of the implant interior and surrounding disc space appropriately.

Figure 2:
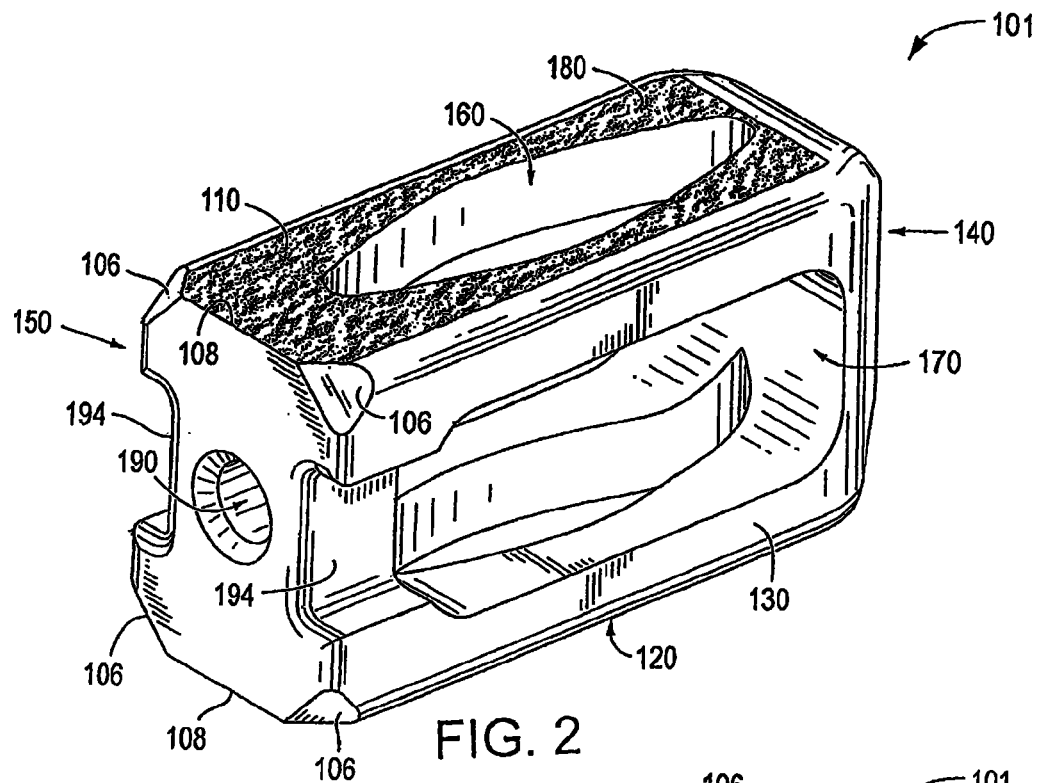
FIG. 2 shows a perspective view from the front of another embodiment of the interbody spinal implant according to the invention.
Figure 3:
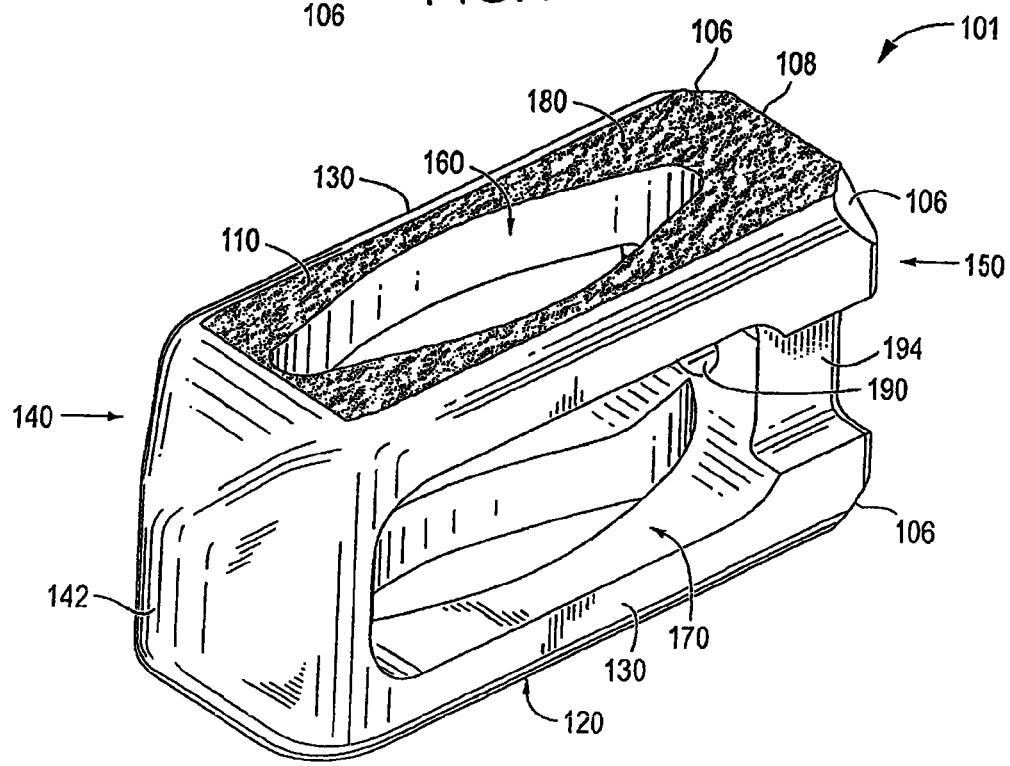
FIG. 3 shows a perspective view from the rear of the embodiment of the interbody spinal implant illustrated in FIG. 2.

As noted above, FIG. 1 shows a perspective view of one embodiment of the invention, the interbody spinal implant 1, which is especially well adapted for use in an ALIF procedure. Other embodiments of the invention are better suited for PLIF, TLIF, or cervical fusion procedures. Specifically, FIGS. 2 and 3 show perspective views, from the front and rear, respectively, of an embodiment of an interbody spinal implant 101 especially well adapted for use in a PLIF procedure. The interbody spinal implant 101 includes a body having a top surface 110, a bottom surface 120, opposing lateral sides 130, and opposing anterior 140 and posterior 150 portions. One or both of the top surface 110 and the bottom surface 120 has a roughened topography 180 for gripping adjacent bone and inhibiting migration of the implant 101.

Certain embodiments of the interbody spinal implant 101 are substantially hollow and have a generally rectangular shape with smooth, rounded, or both smooth and rounded lateral sides and anterior-lateral corners. As best shown in FIG. 3, the anterior portion 140 may have a tapered nose 142 to facilitate insertion of the implant 101. To further facilitate insertion, the implant 101 has chamfers 106 at the corners of its posterior portion 150. The chamfers 106 prevent the implant 101 from catching upon insertion, risking potential damage such as severed nerves, while still permitting the implant 101 to have an anti-expulsion edge 108.

As illustrated in FIG. 2, the implant 101 has an opening 190 in the posterior portion 150. The opening 190 has a number of functions. One function is to facilitate manipulation of the implant 101 by the caretaker. Thus, the caretaker may insert a surgical tool into the opening 190 and, through the engagement between the surgical tool and the opening 190, manipulate the implant 101. The opening 190 may be threaded to enhance the engagement.

The implant 101 may also have an Implant Holding Feature (IHF) 194 instead of or in addition to the opening 190. As illustrated in FIG. 2, the IHF 194 is located proximate the opening 190 in the posterior portion 150. In this particular example, the IHF 194 is a U-shaped notch. Like the opening 190, the IHF 194 has a number of functions, one of which is to facilitate manipulation of the implant 101 by the caretaker. Other functions of the opening 190 and the IHF 194 are to increase visibility of the implant 101 during surgical procedures and to enhance engagement between bone graft material and adjacent bone.

The embodiment of the invention illustrated in FIGS. 2 and 3 is especially well suited for a PLIF surgical procedure. TLIF surgery is done through the posterior (rear) part of the spine and is essentially like an extended PLIF procedure. The TLIF procedure was developed in response to some of the technical problems encountered with a PLIF procedure. The main difference between the two spine fusion procedures is that the TLIF approach to the disc space is expanded by removing one entire facet joint; a PLIF procedure is usually done on both sides by only taking a portion of each of the paired facet joints.

By removing the entire facet joint, visualization into the disc space is improved and more disc material can be removed. Such removal should also provide for less nerve retraction. Because one entire facet is removed, the TLIF procedure is only done on one side: removing the facet joints on both sides of the spine would result in too much instability. With increased visualization and room for dissection, one or both of a larger implant and more bone graft can be used in the TLIF procedure. Theoretically, these advantages can allow the spine surgeon to distract the disc space more and realign the spine better (re-establish the normal lumbar lordosis).

Although the TLIF procedure offers some improvements over a PLIF procedure, the anterior approach in most cases still provides the best visualization, most surface area for healing, and the best reduction of any of the approaches to the disc space. These advantages must be weighed, however, against the increased morbidity (e.g., unwanted aftereffects and postoperative discomfort) of a second incision. Probably the biggest determinate in how the disc space is approached is the comfort level that the spine surgeon has with an anterior approach for the spine fusion surgery. Not all spine surgeons are comfortable with operating around the great vessels (aorta and vena cava) or have access to a skilled vascular surgeon to help them with the approach. Therefore, choosing one of the posterior approaches for the spine fusion surgery is often a more practical solution.

Figure 4:
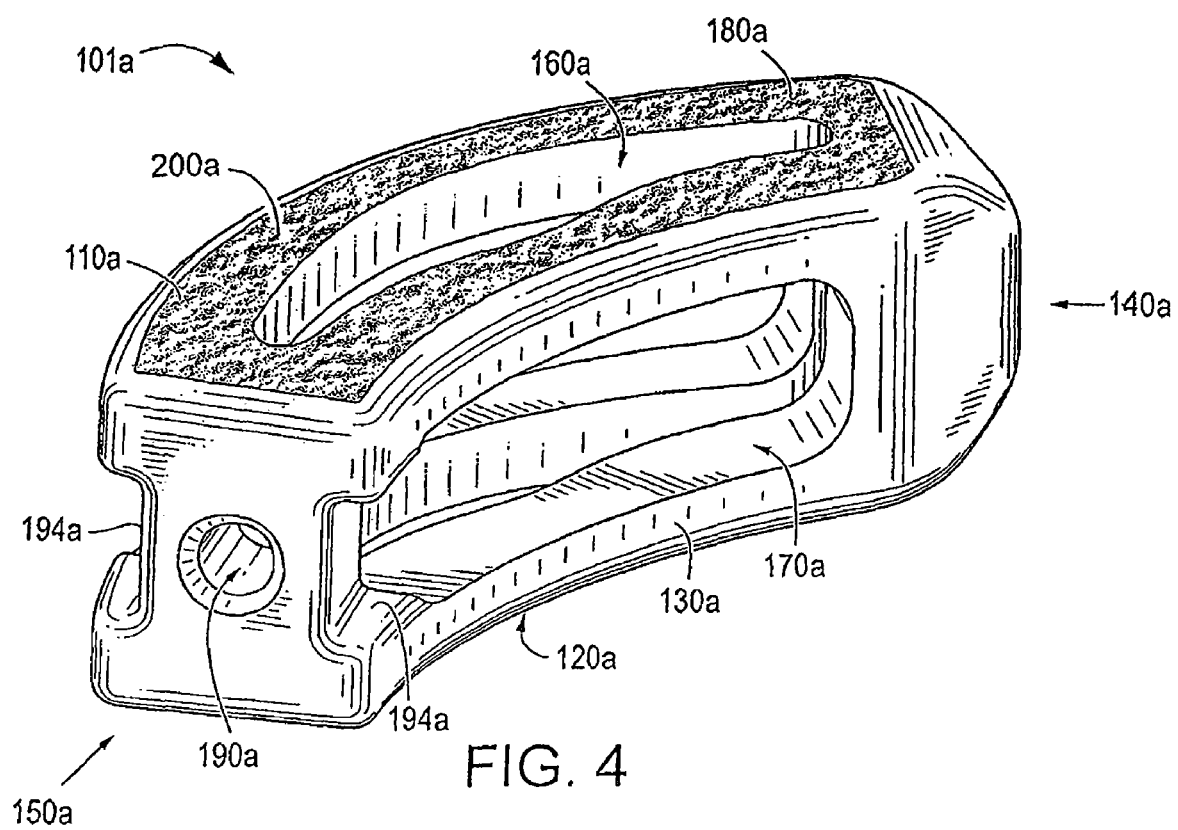
FIG. 4 shows a perspective view from the front of yet another embodiment of the interbody spinal implant according to the invention.
Figure 5:
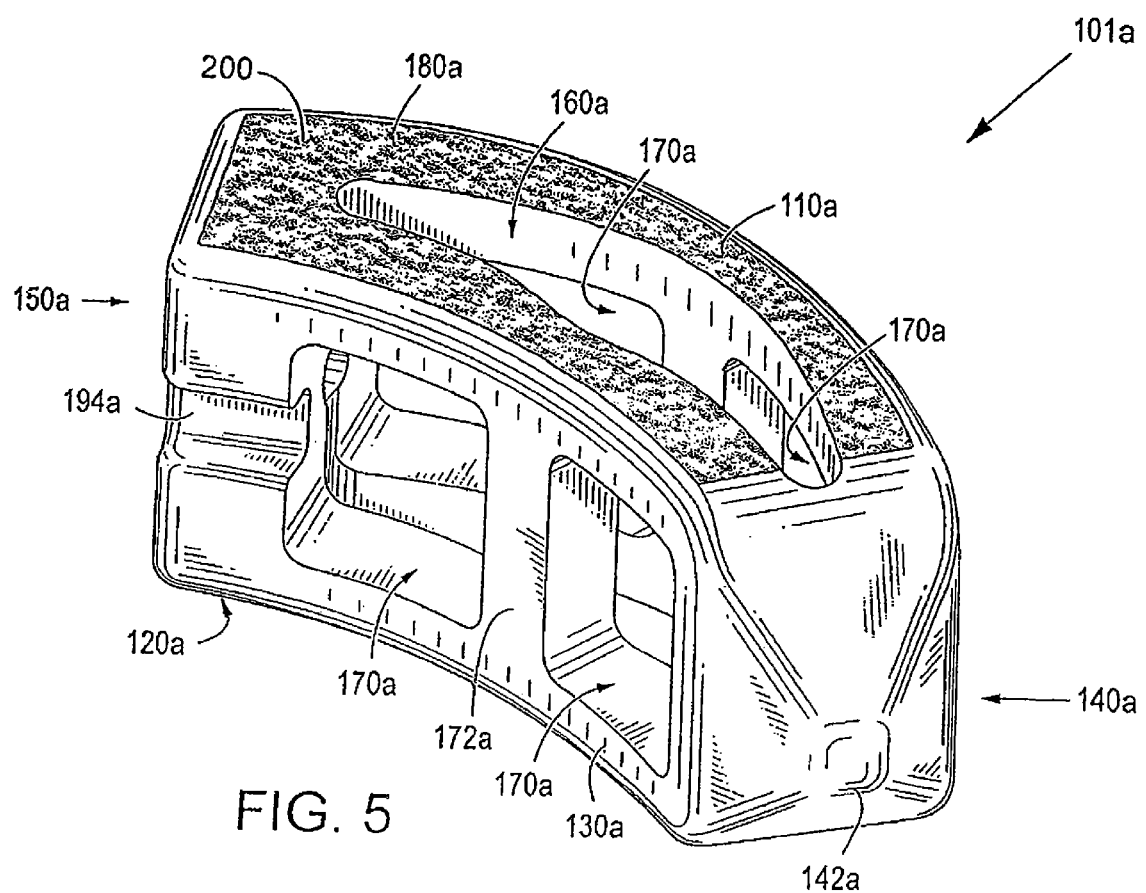
FIG. 5 shows a perspective view from the rear of the embodiment of the interbody spinal implant illustrated in FIG. 4 highlighting an alternative transverse aperture.

The embodiment of the invention illustrated in FIGS. 4 and 5 is especially well suited when the spine surgeon elects a TLIF procedure. Many of the features of the implant 101a illustrated in FIGS. 4 and 5 are the same as those of the implant 101 illustrated in FIGS. 2 and 3. Therefore, these features are given the same reference numbers, with the addition of the letter "a," and are not described further.

There are several differences, however, between the two embodiments. For example, unlike the substantially rectangular shape of the implant 101, the implant 101a has a curved shape. Further, the chamfers 106 and anti-expulsion edge 108 of the implant 101 are replaced by curves or rounded edges for the implant 101a. Still further, the TLIF procedure often permits use of a larger implant 101a which, in turn, may affect the size and shape of the predetermined vertical aperture 160a.

The substantially constant 9 mm width of the transverse rim 200 of the implant 101 is replaced with a larger, curved transverse rim 200a. The width of the transverse rim 200a is 9 mm in the regions adjacent the anterior 140a and posterior 150a portions. That width gradually increases to 11 mm, however, near the center of the transverse rim 200a. The additional real estate provided by the transverse rim 200a (relative to the transverse rim 200) allows the shape of the vertical aperture 160a to change, in cross section, from approximating a football to approximating a boomerang.

The implant 101a may also have a lordotic angle to facilitate alignment. The lateral side 130a depicted at the top of the implant 101a is preferably generally greater in height than the opposing lateral side 130a. Therefore, the implant 101a may better compensate for the generally less supportive bone found in certain regions of the vertebral endplate.

The intermediate wall 172a may be made of the same material as the remainder of the implant 101a (e.g., metal), or it may be made of another material (e.g., PEEK) to form a composite implant 101a. It is also possible to extend the intermediate wall 172a, whether made of metal, PEEK, ultra-high molecular weight polyethylene (UHMWPE), or another material, to eliminate entirely the transverse aperture 170a. Given the reinforcement function of the intermediate wall 172a, the length of the vertical aperture 160a can be extended (as shown in FIG. 5) beyond the top surface 110a and into the anterior portion 140a of the implant 101a.

The top surface 110a of the implant 101a need not include the roughened topography 180a. This difference permits the implant 101a, at least for certain applications, to be made entirely of a non-metal material. Suitable materials of construction for the implant 101a of such a design (which would not be a composite) include PEEK, hedrocel, UHMWPE, other radiolucent soft plastics, and additional materials as would be known to an artisan.

The embodiments of the invention described above are best suited for one or more of the ALIF, PLIF, and TLIF surgical procedures. Another embodiment of the invention is better suited for cervical fusion procedures. This embodiment is illustrated in FIGS. 6 and 7 as the interbody spinal implant 201.

Because there is not a lot of disc material between the vertebral bodies in the cervical spine, the discs are usually not very large. The space available for the nerves is also not that great, however, which means that even a small cervical disc herniation may impinge on the nerve and cause significant pain. There is also less mechanical load on the discs in the cervical spine as opposed to the load that exists lower in the spine. Among others, these differences have ramifications for the design of the implant 201.

The implant 201 is generally smaller in size than the other implant embodiments. In addition, the lower mechanical load requirements imposed by the cervical application typically render a composite implant unnecessary. Therefore, the implant 201 is generally made entirely of metal (e.g., titanium) and devoid of other materials (e.g., PEEK).

Figure 6:
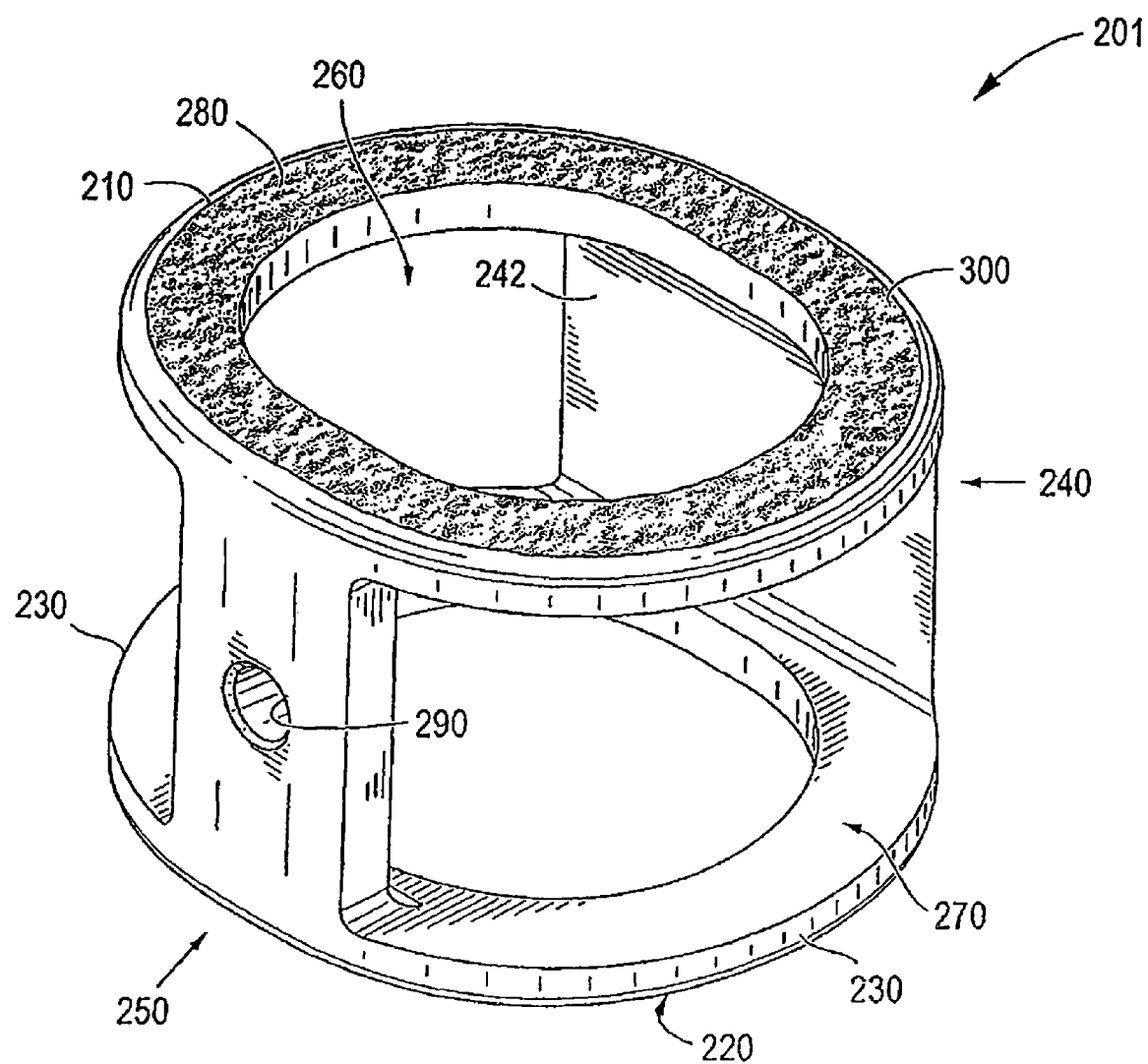
FIG. 6 shows a perspective view of another embodiment of the interbody spinal implant having a generally oval shape and being especially well adapted for use in a cervical spine surgical procedure.
Figure 7:
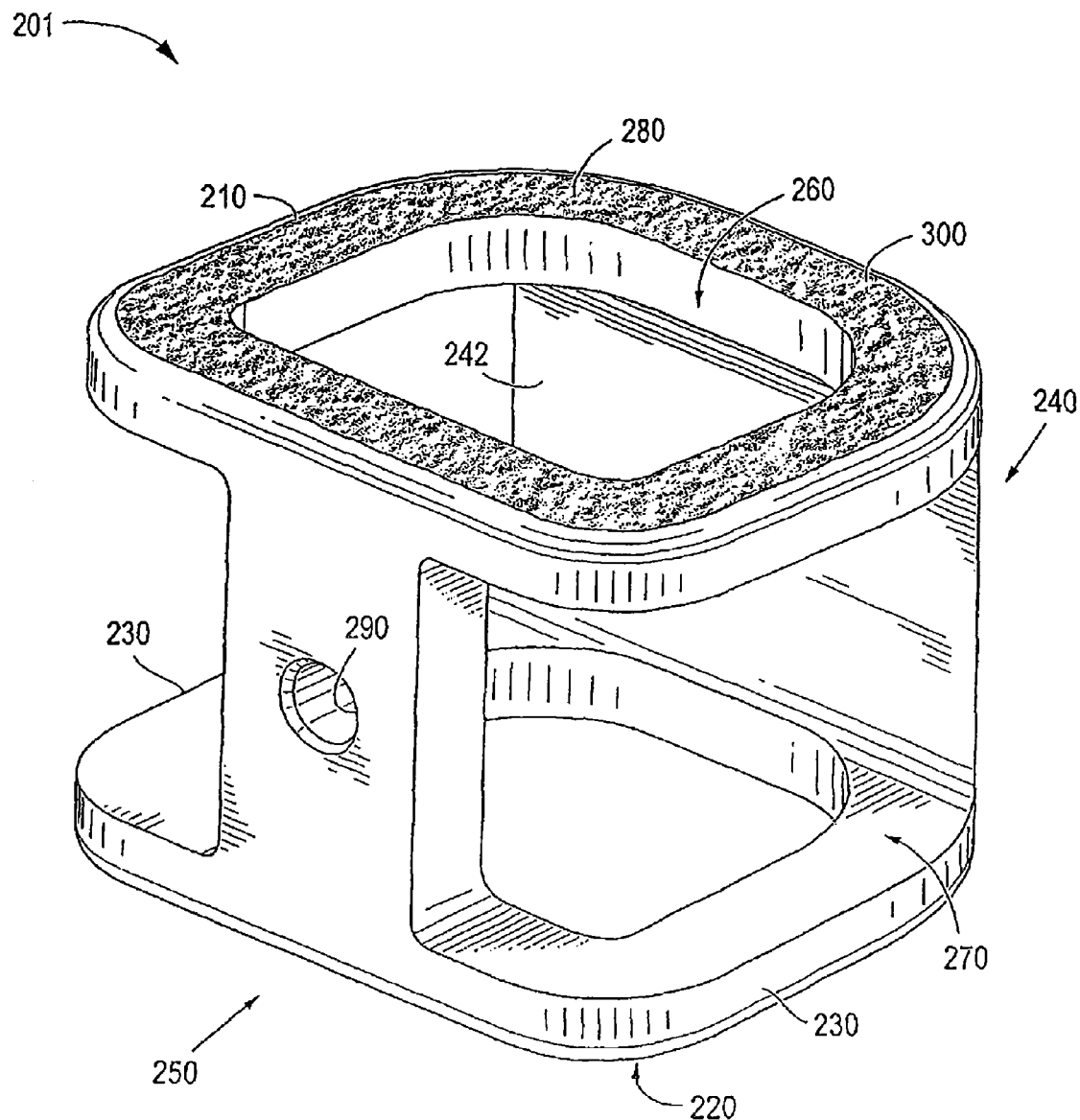
FIG. 7 shows a perspective view of an implant having a generally box shape.
Figure 8:
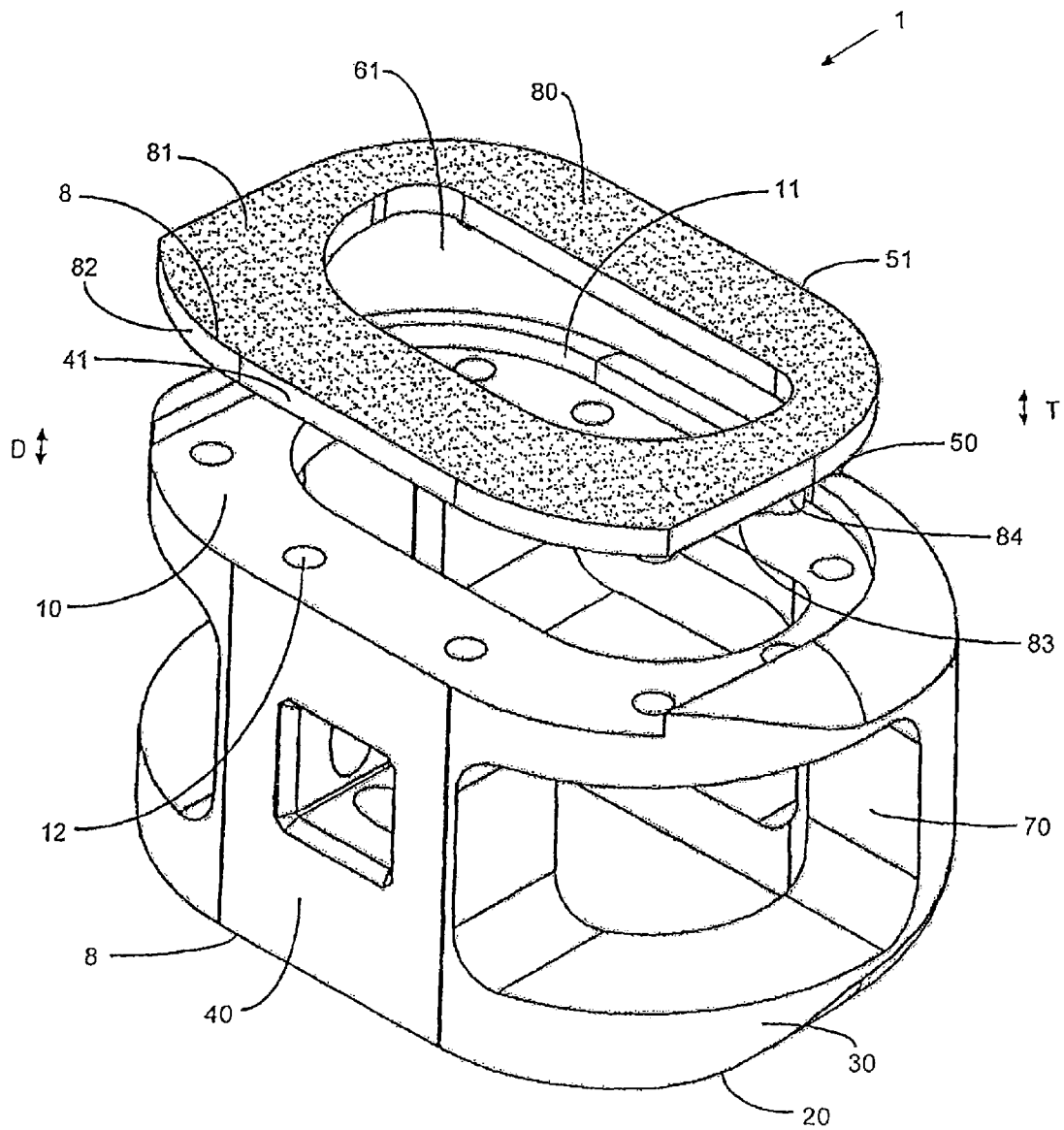
FIG. 8 shows an exploded view of a generally oval-shaped implant with an integration plate.

With specific reference to FIG. 6, the implant 201 includes a body having a top surface 210, a bottom surface 220, opposing lateral sides 230, and opposing anterior 240 and posterior 250 portions. One or both of the top surface 210 and the bottom surface 220 has a roughened topography 280 for gripping adjacent bone and inhibiting migration of the implant 201. The implant 201 is substantially hollow and has a generally oval shape with smooth, rounded, or both smooth and rounded edges.

The implant 201 includes at least one vertical aperture 260 that extends the entire height of the implant body. The vertical aperture 260 further defines a transverse rim 300.

As illustrated in FIG. 6, the implant 201 has an opening 290 in the posterior portion 250. The opening 290 has a number of functions. One function is to facilitate manipulation of the implant 201 by the caretaker. Thus, the caretaker may insert a surgical tool into the opening 290 and, through the engagement between the surgical tool and the opening 290, manipulate the implant 201. The opening 290 may be threaded to enhance the engagement.

As illustrated in FIG. 6, the implant 201 may be provided with a solid rear wall 242. The rear wall 242 extends the entire width of the implant body and nearly the entire height of the implant body. Thus, the rear wall 242 essentially closes the anterior portion 240 of the implant 201. The rear wall 242 may offer one or more of several advantages, including reinforcement of the implant 201 and improved bone graft containment. In the cervical application, it may be important to prevent bone graft material from entering the spinal canal.

Alternative shapes for the implant 201 are possible. As illustrated in FIG. 7, for example, the implant 201 may have a generally box shape which gives the implant 201 increased cortical bone coverage. Like the implant 201 shown in FIG. 6, the implant 201 shown in FIG. 7 has a curved transverse rim 300 in the area of the anterior portion 240. The shape of the posterior portion 250 of the implant 201 is substantially flat, however, and the shape of the transverse rim 300 in the area of the posterior portion 250 is substantially square. Thus, the posterior portion 250 provides a face that can receive impact from a tool, such as a surgical hammer, to force the implant 201 into position.

The implant 201 may also have a lordotic angle to facilitate alignment. As illustrated in FIGS. 6 and 7, the anterior portion 240 is preferably generally greater in height than the posterior portion 250. Therefore, the implant 201 may better compensate for the generally less supportive bone found in certain regions of the vertebral endplate. As an example, four degrees of lordosis may be built into the implant 201 to help restore balance to the spine.

Certain embodiments of the implant 1, 101, 101a, and 201 are generally shaped (i.e., made wide) to maximize contact with the apophyseal rim of the vertebral endplates. They are designed to be impacted between the endplates, with fixation to the endplates created by an interference fit and annular tension. Thus, the implants 1, 101, 101a, and 201 are shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. As much as seven degrees of lordosis (or more) may be built into the implants 1, 101, 101a, and 201 to help restore cervical balance.

When endplate-sparing spinal implant 1, 101, 101a, and 201 seats in the disc space against the apophyseal rim, it should still allow for deflection of the endplates like a diaphragm. This means that, regardless of the stiffness of the spinal implant 1, 101, 101a, and 201, the bone graft material inside the spinal implant 1, 101, 101a, and 201 receives load, leading to healthy fusion. The vertical load in the human spine is transferred though the peripheral cortex of the vertebral bodies. By implanting an apophyseal-supporting inter-body implant 1, 101, 101a, and 201, the natural biomechanics may be better preserved than for conventional devices. If this is true, the adjacent vertebral bodies should be better preserved by the implant 1, 101, 101a, and 201, hence reducing the risk of adjacent segment issues.

In addition, the dual-acid etched roughened topography 80, 180, 180a, and 280 of the top surface 30, 130, 130a, and 230 and the bottom surface 40, 140, 140a, and 240 along with the broad surface area of contact with the end-plates, is expected to yield a high pull-out force in comparison to conventional designs. As enhanced by the sharp edges 8 and 108, a pull-out strength of up to 3,000 nt may be expected. The roughened topography 80, 180, 180a, and 280 creates a biological bond with the end-plates over time, which should enhance the quality of fusion to the bone. Also, the in-growth starts to happen much earlier than the bony fusion. The center of the implant 1, 101, 101a, and 201 remains open to receive bone graft material and enhance fusion. Therefore, it is possible that patients might be able to achieve a full activity level sooner than for conventional designs.

The spinal implant 1, 101, 101a, and 201 according to the invention offers several advantages relative to conventional devices. Such conventional devices include, among others, ring-shaped cages made of allograft bone material, threaded titanium cages, and ring-shaped cages made of PEEK or carbon fiber.

Figure 9:
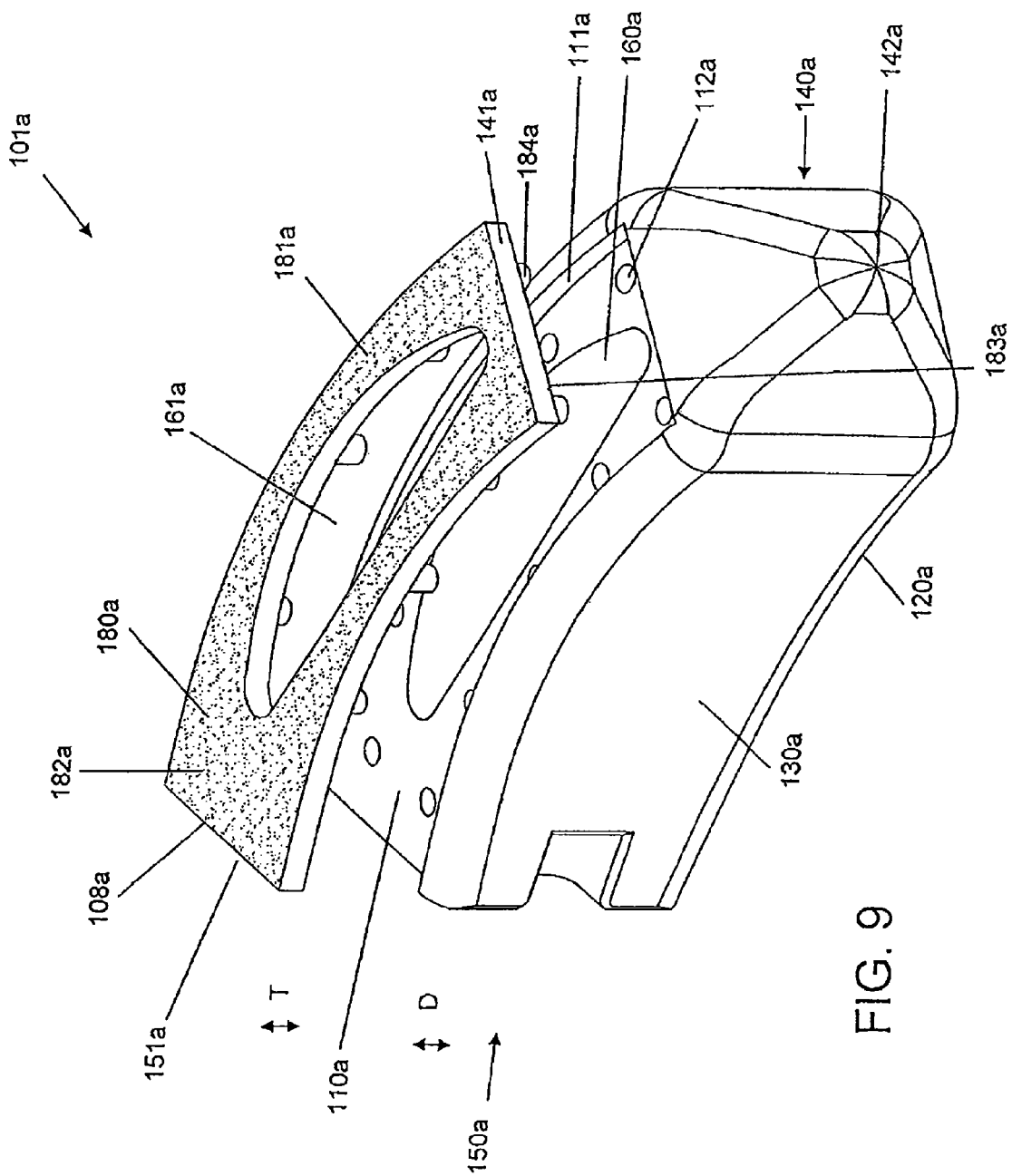
FIG. 9 shows an exploded view of a curved implant with an integration plate.
Figure 10:
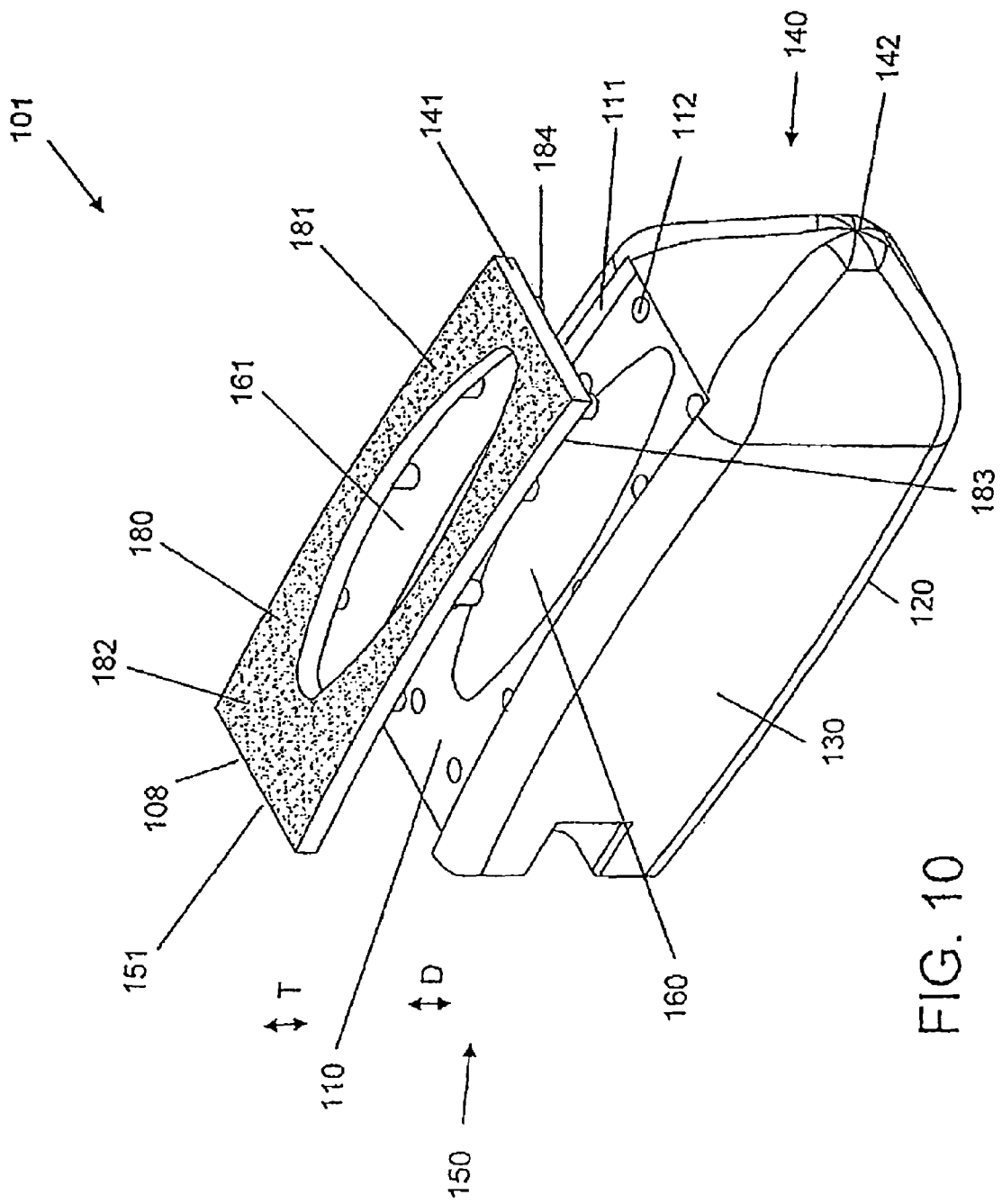
FIG. 10 shows an exploded view of a posterior implant with an integration plate.
Figure 11:
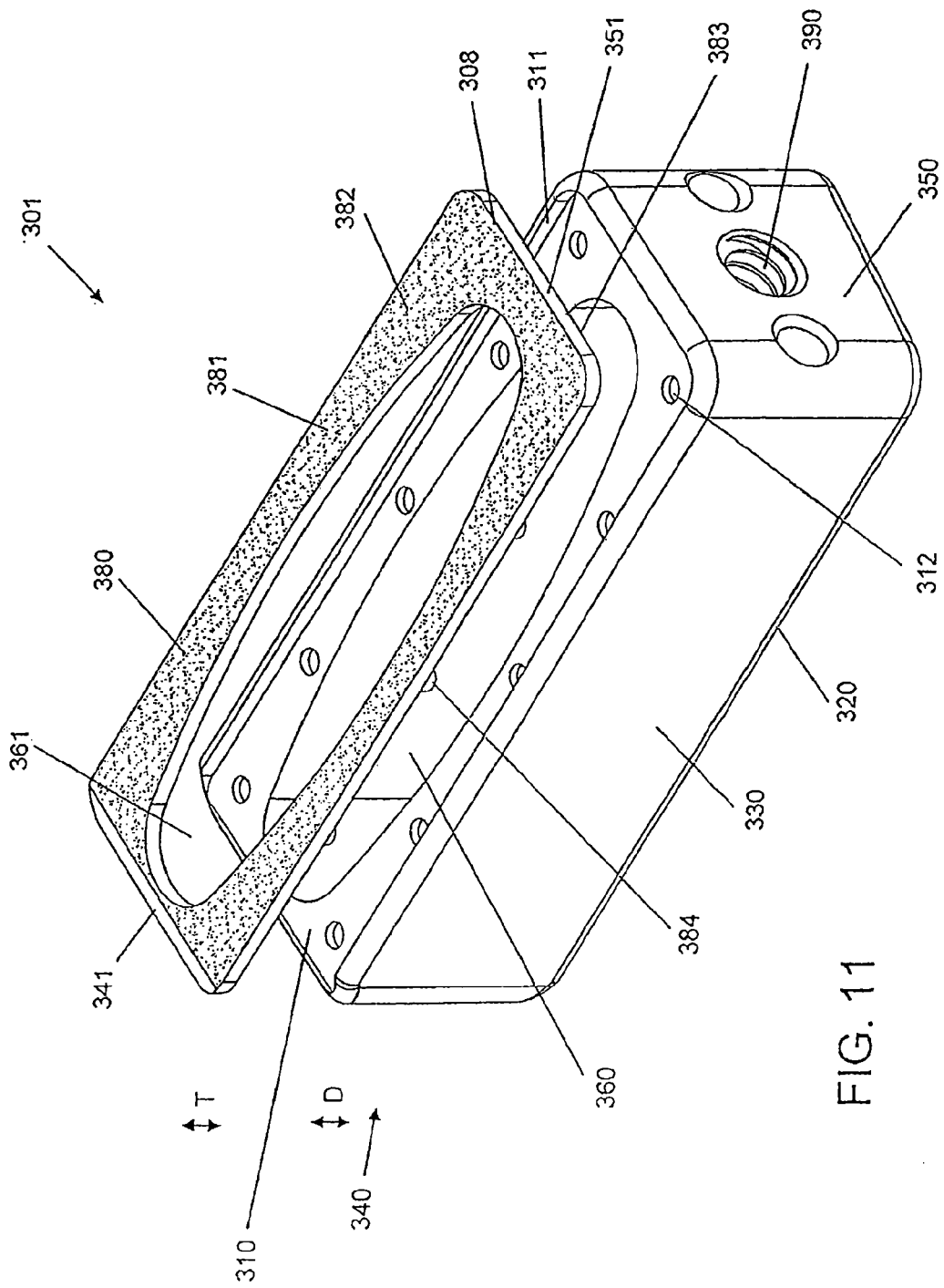
FIG. 11 shows an exploded view of a lateral lumbar implant with an integration plate.

In some aspects, the implant 1, 101, 101a, and 201 includes an integration plate 82, 182, 182a, and 282, for example, as shown in FIG. 8A-FIG. 10 and FIG. 12. In addition, a lateral implant 301 having a substantially rectangular shape may include an integration plate 382, for example, as shown in FIG. 11. The lateral implant 301 comprises the same general features as the implant 1, 101, 101a, and 201, including a top surface 310, a bottom surface 320, lateral sides 330, opposing anterior 340 and posterior 350 portions, an opening 390, as well as at least one vertical aperture 360 that extends the entire height of the implant body.

The integration plate, shown in the drawings as component 82 (FIG. 8A and FIG. 8B), 182 (FIG. 10), 182a (FIG. 9), 382 (FIG. 11), and 282 (FIG. 12), respectively, includes the roughened surface topography 80, 180, 180a, 280, and 380, and is connectable to either or both of the top surface 10, 110, 110a, 210, and 310 or bottom surface 20, 120, 120a, 220, and 320. The integration plate 82, 182, 182a, 282, and 382 includes a top surface 81, 181, 181a, 281, and 381; a bottom surface 83, 183, 183a, 283, and 383; an anterior portion 41, 141, 141a, 241, and 341; a posterior portion 51, 151, 151a, 251, and 351; and at least one vertical aperture 61, 161, 161a, 261, and 361. The anterior portion 41, 141, 141a, 241, and 341 preferably aligns with the anterior portion 40, 140, 140a, 240, and 340 of the main body of the implant 1, 101, 101a, 201, and 301, respectively, and the posterior portion 51, 151, 151a, 251, and 351 aligns with the posterior portion 50, 150, 150a, 250, and 350 of the main body of the implant 1, 101, 101a, 201, and 301, respectively. The vertical aperture 61, 161, 161a, 261, and 361 preferably aligns with the vertical aperture 60, 160, 160a, 260, and 360 of the main body of the implant 1, 101, 101a, 201, and 301, respectively. Thus, the integration plate vertical aperture 61, 161, 161a, 261, and 361 and the body vertical aperture 60, 160, 160a, 260, and 360 preferably comprise substantially the same shape.

The top surface 81, 181, 181a, 281, and 381 of the integration plate 82, 182, 182a, 282, and 382 preferably comprises the roughened topography 80, 180, 180a, 280, and 380. The bottom surface 83, 183, 183a, 283, and 383 of the integration plate 82, 182, 182a, 282, and 382 preferably comprises a reciprocal connector structure, such as a plurality of posts 84, 184, 184a, 284, and 384 that align with and insert into a corresponding connector structure such as a plurality of holes 12, 112, 112a, 212, and 312 on the top surface 10, 110, 110a, 210, and 310 and/or bottom surface 20, 120, 120a, 220, and 320 of the main body of the implant 1, 101, 101a, 201, and 301, respectively, and thus facilitate the connection between the integration plate 82, 182, 182a, 282, and 382 and the main body of the implant 1, 101, 101a, 201, and 301. Thus, integration plates 82, 182, 182a, 282, and 382 with different sizes, shapes, or features may be used in connection with the implant 1, 101, 101a, 201, and 301, for example, to accommodate attributes of the spine of the patient to which the implant 1, 101, 101a, 201, and 301 is to be implanted. Among these different sizes, shapes, and features are lordotic angles; anti-expulsion edges 8, 108, 108a, 208, and 308; and anti-expulsion angles as described throughout this specification.

The implant 1, 101, 101a, 201, and 301 is configured to receive the integration plate 82, 182, 182a, 282, and 382, respectively. Thus, for example, the top surface 10, 110, 110a, 210, and 310 and/or bottom surface 20, 120, 120a, 220, and 320 of the implant 1, 101, 101a, 201, and 301 may be recessed, and comprise a plurality of holes 12, 112, 112a, 212, and 312 that mate with the plurality of posts 84, 184, 184a, 284, and 384 on the bottom surface 83, 183, 183a, 283, and 383 of the integration plate 82, 182, 182a, 282, and 382. Thus, the plurality of posts 84, 184, 184a, 284, and 384 are inserted into the plurality of holes 12, 112, 112a, 212, and 312.

Figure 12:
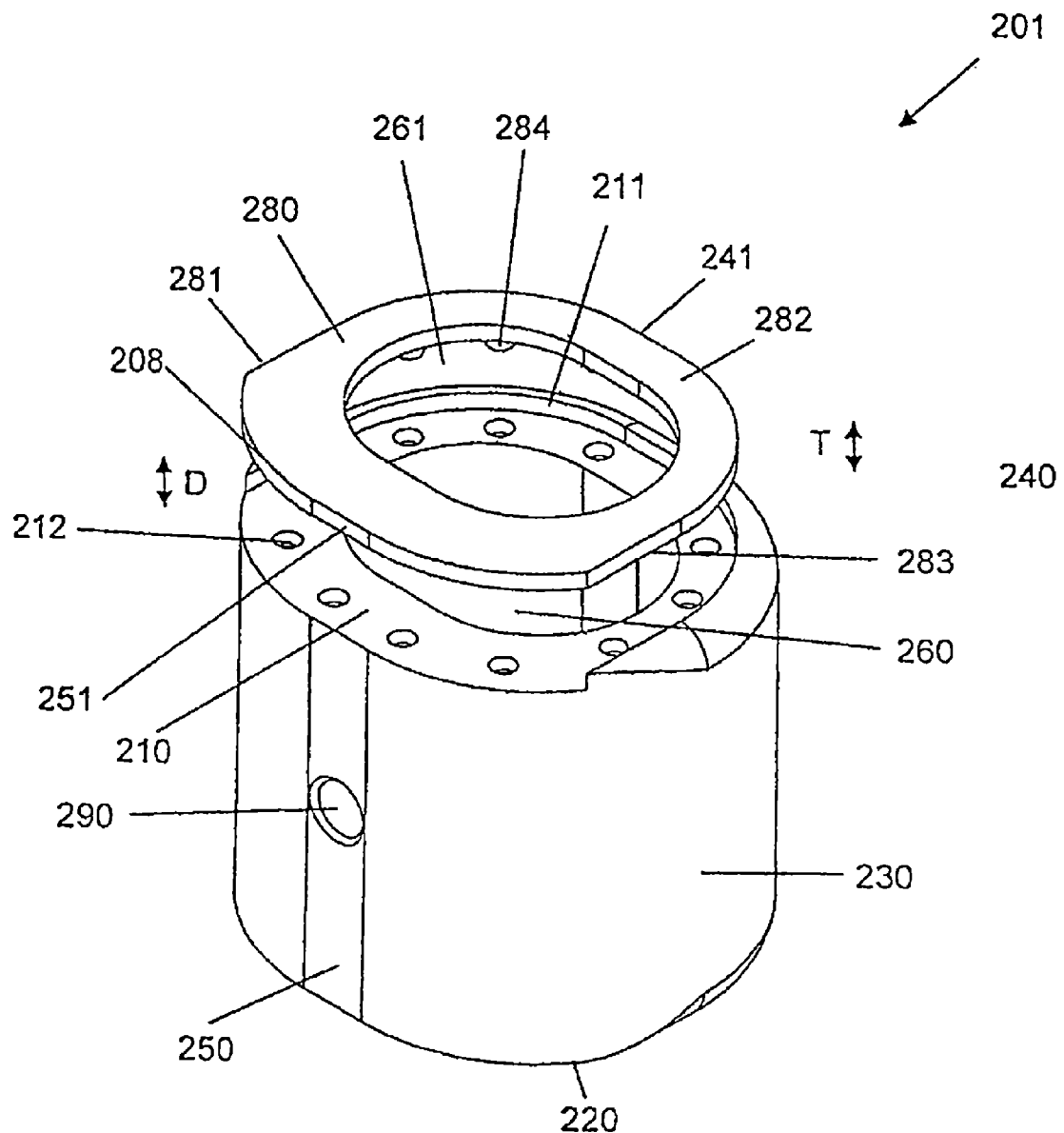
FIG. 12 shows an exploded view of a generally oval-shaped anterior cervical implant with an integration plate.

FIG. 8A and FIG. 8B show that the top surface 10 is recessed and comprises a plurality of holes 12, but the recessed bottom surface 20 and its holes 12 are not shown. FIG. 9 shows that the top surface 110a is recessed and comprises a plurality of holes 112a, but the recessed bottom surface 120a and its holes 112a are not shown. FIG. 10 shows that the top surface 110 is recessed and comprises a plurality of holes 112, but the recessed bottom surface 120 and its holes 112 are not shown. FIG. 11 shows that the top surface 310 is recessed and comprises a plurality of holes 312, but the recessed bottom surface 320 and its holes 312 are not shown. FIG. 12 shows that the top surface 210 is recessed and comprises a plurality of holes 212, but the recessed bottom surface 220 and its holes 212 are not shown. The recess may be at a depth D, and the recess depth D preferably is uniform throughout the top surface 10, 110, 110a, 210, and 310 and/or bottom surface 20, 120, 120a, 220, and 320.

The recess depth D preferably corresponds to a thickness T of the integration plate 82, 182, 182a, 282, and 382. Thus, in some aspects, the depth D and thickness T are the same so that once the integration plate 82, 182, 182a, 282, and 382 and body of the implant 1, 101, 101a, 201, and 301, respectively, are placed together, the top surface 10, 110, 110a, 210, and 310 and/or bottom surface 20, 120, 120a, 220, and 320 of the implant 1, 101, 101a, 201, and 301 is substantially even, at least at the seam/junction between the integration plate 82, 182, 182a, 282, and 382 and the top surface 10, 110, 110a, 210, and 310 or bottom surface 20, 210, 120a, 220, and 320. In some embodiments, the posterior portion 51, 151, 151a, 251, and 351 and the anterior portion 41, 141, 141a, 241, and 341 of the integration plate 82, 182, 182a, 282, and 382 have different thicknesses such that the anterior portion 41, 141, 141a, 241, and 341 has a greater thickness than the thickness T of the posterior portion 51, 151, 151a, 251, and 351.

The recess depth D, the thickness T, and the thickness T' may each independently be from about 0.1 mm to about 10 mm. In preferred aspects, the recess depth D, the thickness T, and the thickness T' may each independently be from about 1 mm to about 5 mm. Thus, for example, either the recess depth D, the thickness T, and the thickness T' may be selected from about 0.1 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, 5.5 mm, about 6 mm, about 6.5 mm, about 7 mm, about 75 mm, or about 8 mm.

Recessing the top surface 10, 110, 110a, 210, and 310 or bottom surface 20, 120, 120a, 220, and 320 exposes a ridge 11, 111, 111a, 211, and 311 against which the anterior portion 41, 141, 141a, 241, and 341, posterior portion 51, 151, 151a, 251, and 251 or lateral side of the integration plate 82, 182, 182a, 282, and 382 may be seated when brought together with the implant 1, 101, 101a, 201, and 301.

The integration plate 82, 182, 182a, 282, and 382 may be used with an implant suitable for ALIF (e.g., implant 1, integration plate 82), PLIF (e.g., implant 101, integration plate 182), or TLIF fusion (e.g., implant 101a, integration plate 182a); may be used with an implant suitable for cervical fusion (e.g., implant 201, integration plate 282); and may be used with an implant suitable for lateral lumbar insertion (e.g., implant 301, integration plate 382). The integration plate 82, 182, 182a, 282, and 382 is preferably metal, and may be used with a metal implant. The metal integration plate 82, 182, 182a, 282, and 382 may also be used with a molded plastic or polymer implant, or a composite implant. In some aspects, the integration plate 82, 182, 182a, 282, and 382 may also comprise a plastic, polymeric, or composite material.

The reciprocal connector such as the post 84, 184, 184a, 284, and 384 preferably is secured within the connector of the body such as the hole 12, 112, 112a, 212, and 312 to mediate the connection between the integration plate 82, 182, 182a, 282, and 382 and the implant 1, 101, 101a, 201, and 301. The connection should be capable of withstanding significant loads and shear forces when implanted in the spine of the patient. The connection between the post 84, 184, 184*a*, 284, and 384 and the hole 12, 112, 112*a*, 212, and 312 may comprise a friction fit. In some aspects, an adhesive may be used to further strengthen any of the integration plate 82, 182, 182*a*, 282, and 382 and implant 1, 101, 101*a*, 201, and 301 connections. An adhesive may comprise a cement, glue, polymer, epoxy, solder, weld, or other suitable binding material.

In some aspects, the shape of the vertical aperture 60, 160, 160*a*, 260, and 360 and/or the shape of the integration plate vertical aperture 61, 161, 161*a*, 261, and 361 may be varied. For example, the shape may be substantially circular, elliptical, or D-shaped. In some aspects, the anterior, posterior, or lateral sides of the circle, ellipse, or D-shape may bow outward (e.g., a rhomboid oval) or inward (e.g., hourglass shape). The shape may also include straight edges, including a substantially diamond, triangular, rectangular, quadrilateral, or polygonal shape, including a star shape. The shape may comprise an irregular shape or form. The particular shape may be based on the insertion path of the implant 1, 101, 101*a*, 201, and 301 and/or the final location and orientation in the disc space. The shape of the vertical aperture 60, 160, 160*a*, 260, and 360 and/or the shape of the integration plate vertical aperture 61, 161, 161*a*, 261, and 361 may also be based on the frictional characteristics of the roughened surface topography 80, 180, 180*a*, 280, and 380. The implant vertical aperture 60, 160, 160*a*, 260, and 360 preferably aligns with the integration plate vertical aperture 61, 161, 161*a*, 261, and 361.

Each implant body vertical aperture 60, 160, 160*a*, 260, and 360 and integration plate vertical aperture 61, 161, 161*a*, 261, and 361 preferably has substantially the same length, substantially the same width, substantially the same shape, and substantially the same location on their respective surfaces. Nevertheless, in some aspects, the integration plate vertical aperture 61, 161, 161*a*, 261, and 361 may be longer and/or wider and/or positioned differently than its implant vertical aperture 60, 160, 160*a*, 260, and 360 counterpart. For example, the vertical aperture 60, 160, 160*a*, 260, and 360 may be narrower in terms of length and width relative to the integration plate vertical aperture 61, 161, 161*a*, 261, and 361 (which are comparatively larger) such that the graft material occupies a wider surface area at its top or bottom relative to the center mass. Such a configuration may be desirable for purposes of using less bone graft material by lessening the inner volume of the implant 1, 101, 101*a*, 201, and 301 to be filled with bone graft material. For example, the inner volume of the implant 1, 101, 101*a*, 201, and 301 may comprise a "V" shape, or an "X" or hourglass shape.

In some aspects, the implant 1, 101, 101*a*, 201, and 301 comprises an integration plate 82, 182, 182*a*, 282, and 382 on either or both of the top surface 10, 110, 110*a*, 210, and 310 and bottom surface 20, 120, 120*a*, 220, and 320, having a vertical aperture 61, 161, 161*a*, 261, and 361. Thus, the bone graft material is loaded into the vertical aperture 61, 161, 161*a*, 261, and 361 of the integration plate 82, 182, 182*a*, 282, and 382 and the vertical aperture 60, 160, 160*a*, 260, and 360 of the implant 1, 101, 101*a*, 201, and 301. Accordingly, bone graft material housed in the implant 1, 101, 101*a*, 201, and 301 may extend through the implant vertical aperture 60, 160, 160*a*, 260, and 360 and through the integration plate vertical aperture 61, 161, 161*a*, 261, and 361.

One or more of the anterior 40, 140, 140*a*, 240, and 340 edges, posterior 50, 150, 150*a*, 250, and 350 edges, and lateral side 30, 130, 130*a*, 230, and 330 edges of the implant may be rounded or tapered (see, e.g., FIG. 1A-FIG. 7). The rounding or tapering is preferably present on at least the insertion face of the implant 1, 101, 101*a*, 201, and 301. The rounding or tapering may facilitate insertion of the implant 1, 101, 101*a*, 201, and 301 by lessening friction or the possibility of snagging vertebral endplate bone as the implant 1, 101, 101*a*, 201, and 301 is placed and positioned in the intervertebral space. As well, the rounding or tapering may help to avoid snagging or damaging blood vessels and nerves in and around the insertion site.

The vertical aperture 60, 160, 160*a*, 260, and 360, and the integration plate vertical aperture 61, 161, 161*a*, 261, and 361 each preferably comprises a maximum width at its center. The width of the vertical aperture 60, 160, 160*a*, 260, and 360, and the integration plate vertical aperture 61, 161, 161*a*, 261, and 361 may range from about 20% to about 80% of the distance between opposing lateral sides. In some aspects, the width ranges from about 40% to about 80% of the distance between the opposing lateral sides. In some aspects, the width ranges from about 50% to about 70% of the distance between the opposing lateral sides. In some aspects, the width ranges from about 50% to about 65% of the distance between the opposing lateral sides. In some aspects, the width ranges from about 60% to about 70% of the distance between the opposing lateral sides. In some aspects, the width ranges from about 55% to about 75% of the distance between the opposing lateral sides. In some aspects, the width ranges from about 60% to about 80% of the distance between the opposing lateral sides. In some aspects, the width is about 40%, about 45%, about 50%, about 55%, about 60%, about 65%, about 70%, about 75%, about 80%, about 85%, or about 90% of the distance between the opposing lateral sides. Preferably, the width of the vertical aperture 60, 160, 160*a*, 260, and 360, or the integration plate vertical aperture 61, 161, 161*a*, 261, and 361 comprises the dimension between the lateral sides.

The length of the vertical aperture 60, 160, 160*a*, 260, and 360, and the integration plate vertical aperture 61, 161, 161*a*, 261, and 361 may range from about 20% to about 80% of the distance between the anterior and posterior edges. In some aspects, the length ranges from about 40% to about 80% of the distance between the anterior and posterior edges. In some aspects, the length ranges from about 50% to about 70% of the distance between the anterior and posterior edges. In some aspects, the length ranges from about 50% to about 65% of the distance between the anterior and posterior edges. In some aspects, the length ranges from about 60% to about 70% of the distance between the anterior and posterior edges. In some aspects, the length ranges from about 55% to about 75% of the distance between the anterior and posterior edges. In some aspects, the length ranges from about 60% to about 80% of the distance between the anterior and posterior edges. In some aspects, the length is about 40%, about 45%, about 50%, about 55%, about 60%, about 65%, about 70%, about 75%, about 80%, about 85%, or about 90% of the distance between the anterior and posterior edges. Preferably, the length of the vertical aperture 60, 160, 160*a*, 260, and 360, or the integration plate vertical aperture 61, 161, 161*a*, 261, and 361 comprises the dimension between the anterior and posterior edges. The size of the length and the size of the width of the vertical aperture 60, 160, 160*a*, 260, and 360, or the integration plate vertical aperture 61, 161, 161*a*, 261, and 361 may vary independently of each other.

The implant 1, 101, 101*a*, 201, and 301 may include at least one transverse aperture 70, 170, 170*a*, 270, and 370 that extends the entire transverse length of the implant body. The transverse aperture 70, 170, 170*a*, 270, and 370 may help improve the visibility of the implant 1, 101, 101*a*, 201, and 301 during a surgical procedure to ensure proper implant placement and seating, and to improve post-operative assessment of implant fusion, and (b) to facilitate engagement between bone graft material and adjacent bone. As well, the transverse aperture 70, 170, 170a, 270, and 370 may be used to fill the hollow center of the implant 1, 101, 101a, 201, and 301 with a bone graft material, or to add additional bone graft material when the implant 1, 101, 101a, 201, and 301 is set in position during the implantation procedure. Once the hollow center is filled, the bone graft material may flow out from the vertical aperture 60, 160, 160a, 260, and 360 and/or integration plate vertical aperture 61, 161, 161a, 261, and 361, as well as one or more of the transverse apertures 70, 170, 170a, 270, and 370.

As shown in FIG. 1A and FIGS. 2-7 and 3, the transverse aperture 70, 170, 170a, 270, and 370 may extend the entire transverse length of the implant body, and may extend nearly the entire height of the implant body. Like the vertical aperture 60, 160, 160a, 260, and 360, the size and shape of the transverse aperture 70, 170, 170a, 270, and 370 are carefully chosen (or predetermined) to achieve a preferable design tradeoff for the particular application envisioned for the implant 1, 101, 101a, 201, and 301. In some embodiments, the size and shape of the transverse aperture 70, 170, 170a, 270, and 370 approach the maximum possible dimensions. The transverse aperture 70, 170, 170a, 270, and 370 preferably comprises minimal dimensions to maximize the strength and structural integrity of the implant 1, 101, 101a, 201, and 301. Suitable shapes may be a substantially circular, elliptical, D-shaped, triangular, quadrilateral, rectangular, or polygonal shape.

In some embodiments, the transverse aperture 70, 170, 170a, 270, and 370 may be broken into two, separate sections by an intermediate wall 72, 172, 172a, 272, and 372. See, e.g., FIG. 5, which shows the intermediate wall 172a (the intermediate wall 72, 172, 272, and 372 are not shown). The intermediate wall 72, 172, 172a, 272, and 372 may be made of the same material as the implant 1, 101, 101, 101a, 201, and 301 (e.g., metal, polymer, or composite). The intermediate wall 72, 172, 172a, 272, and 372 may offer one or more of several advantages, including reinforcement of the implant 1, 101, 101a, 201, and 301 and improved bone graft containment.

Figure 13A:
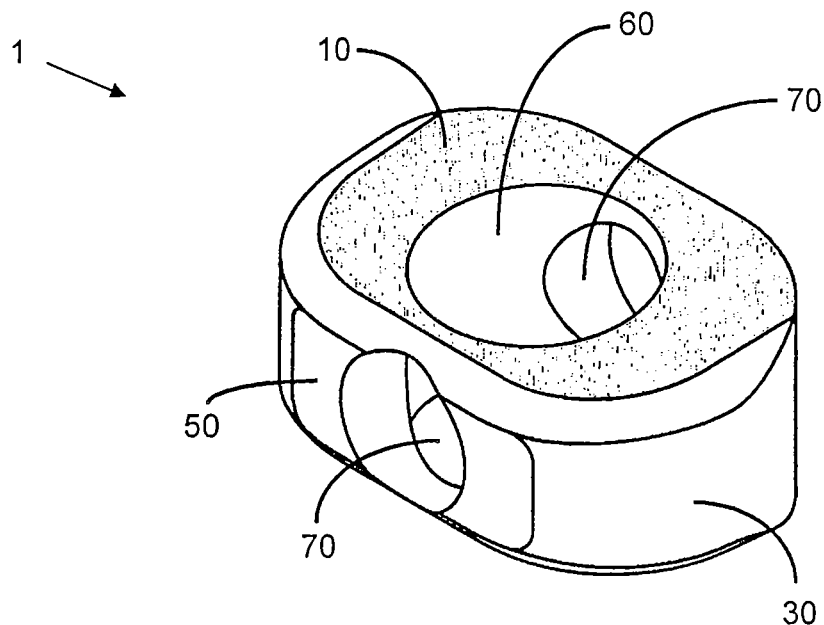
FIG. 13A shows a posterior perspective of an oval-shaped implant having a transverse aperture on the posterior face.
Figure 13B:
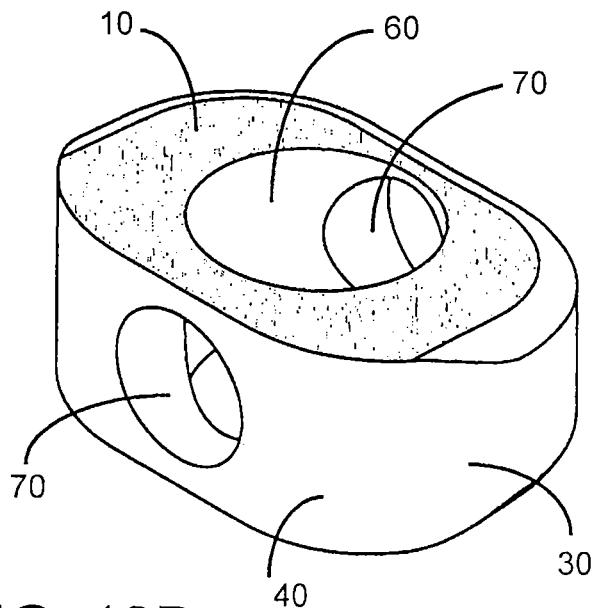
FIG. 13B shows an anterior perspective of an oval-shaped implant, and shows the implant having a transverse aperture on the anterior face.
Figure 13C:
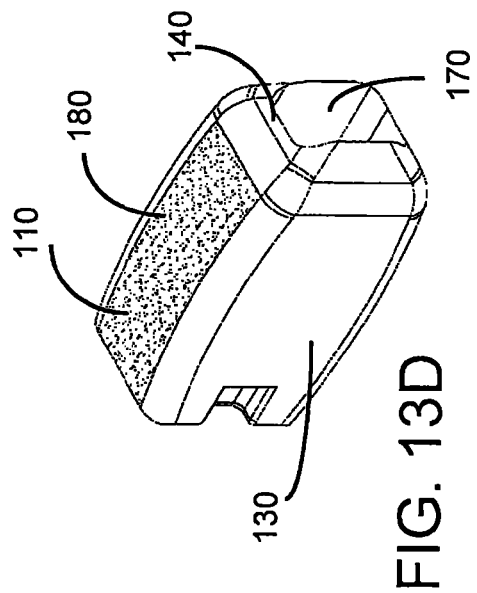
FIG. 13C shows a perspective of a posterior implant having a transverse aperture on the posterior face.
Figure 13D:
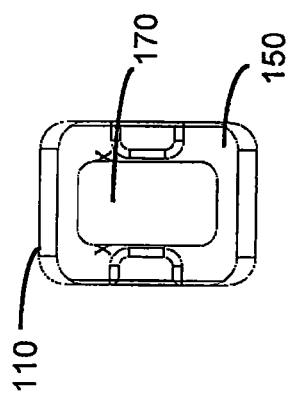
FIG. 13D shows another perspective of a posterior implant, and shows the implant having a transverse aperture on the anterior face.
Figure 13E:
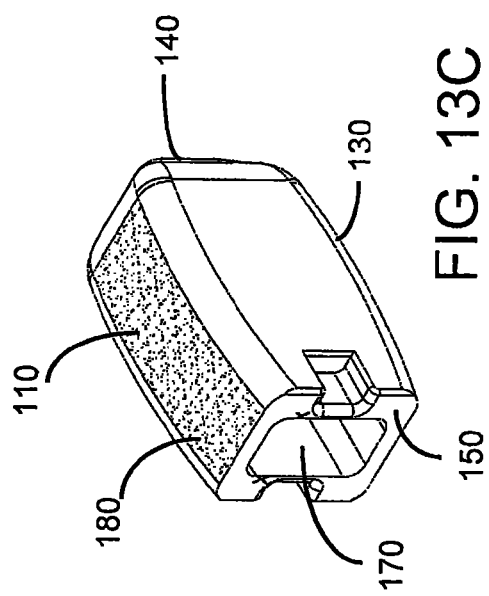
FIG. 13E shows a view of the anterior transverse aperture of a posterior implant.
Figure 13F:
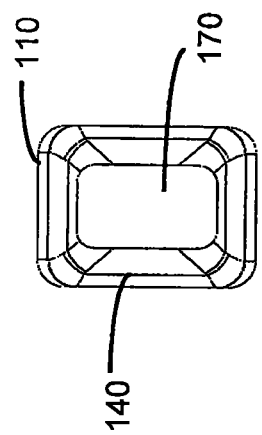
FIG. 13F shows a view of the posterior transverse aperture of a posterior implant.

Various configurations, including various shapes, dimensions, position, location, and quantity of the transverse aperture 70, 170, 170a, 270, and 370 are possible. FIG. 13A and FIG. 13B show an example of an oval-shaped implant having a circular transverse aperture 70 on the posterior portion 50 and on the anterior portion 40. FIG. 13C and FIG. 13D show an example of a posterior implant having a transverse aperture 170 on the posterior portion 150 and on the anterior portion 150. FIG. 13E shows the quadrilateral transverse aperture 170 on the anterior portion 140, and FIG. 13F shows the quadrilateral transverse aperture 170 on the posterior portion 150. FIG. 13A and FIG. 13B also illustrate that the implant 1 (also implant 101, 101a, 201, and 301) may include a single vertical aperture 60 (also 160, 160a, 260, and 360), and in FIG. 13C and FIG. 13D illustrate that the implant 101 (also implant 1, 101a, 201, and 301) need not include a single vertical aperture 160. In some aspects, the implant 1, 101, 101a, 201, and 301 includes a transverse aperture 70, 170, 170a, 270, and 370 on either the posterior portion 50, 150, 150a, 250, and 350 or the anterior portion 40, 140, 140a, 240, and 340, but not both.

The dimensions of the transverse aperture 70, 170, 170a, 270, and 370 on the posterior portion 50, 150, 150a, 250, and 350 may, for example, be smaller in size than the counterpart dimensions of the transverse aperture 70, 170, 170a, 270, and 370 on the anterior portion 40, 140, 140a, 240, and 340, or vice versa. As well, the dimensions of the transverse aperture 70, 170, 170a, 270, and 370 may be the same on each of the posterior portion 50, 150, 150a, 250, and 350 and the anterior portion 40, 140, 140a, 240, and 340 of the implant 1, 101, 101a, 201, and 301. Different shapes are possible, including an elliptical shape, a rectangular shape, a square shape, a rhomboid shape, a parallelogram shape, a triangular shape, or a polygonal shape of any suitable number of sides. Different shapes, as well as different dimensions of the same or different shapes, may be independently used on the posterior portion 50, 150, 150a, 250, and 350 and the anterior portion 40, 140, 140a, 240, and 340.

Figure 14A:
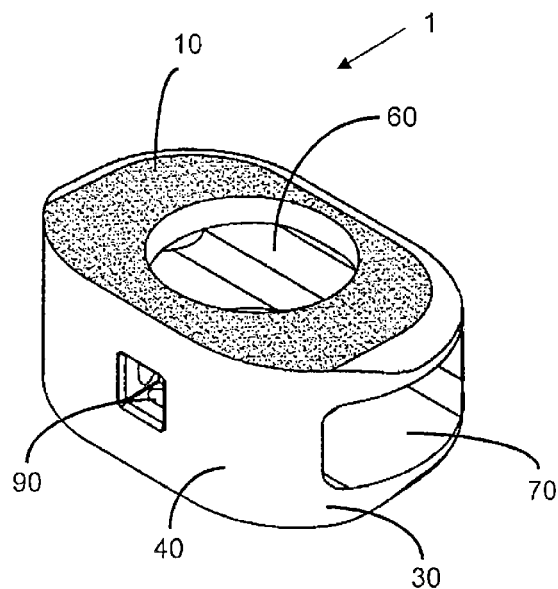
FIG. 14A shows a perspective of an oval-shaped implant having a transverse aperture extending from a lateral side.
Figures 14B, 14C:
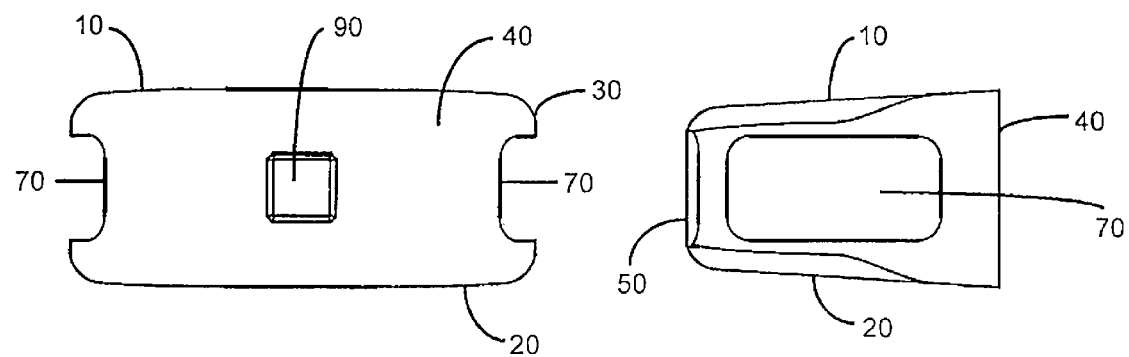
FIG. 14B shows a view of the anterior portion of the oval-shaped implant, and shows the transverse apertures on the lateral sides.
FIG. 14C shows a view of a lateral side of the oval-shaped implant, and shows the transverse aperture.
Figure 14D:
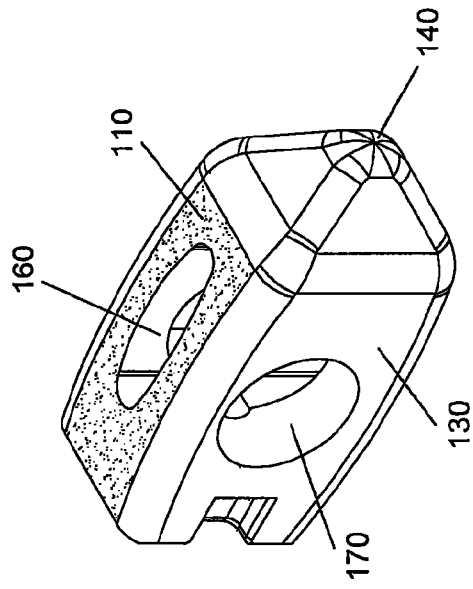
FIG. 14D shows a perspective of a posterior implant, and shows the implant having a transverse aperture on each lateral side, but not the posterior portion.
Figure 14E:
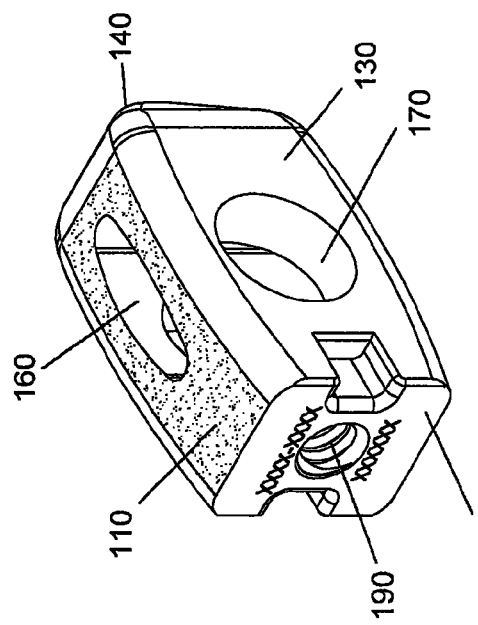
FIG. 14E shows a perspective of a posterior implant, and shows the implant having a transverse aperture on each lateral side, but not the anterior portion.
Figure 14F:
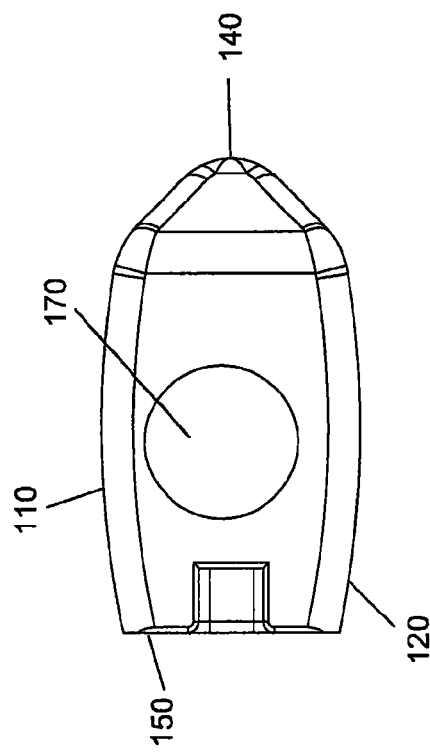
FIG. 14F shows a side perspective of a posterior implant, and shows the lateral side transverse aperture.
Figure 14H:
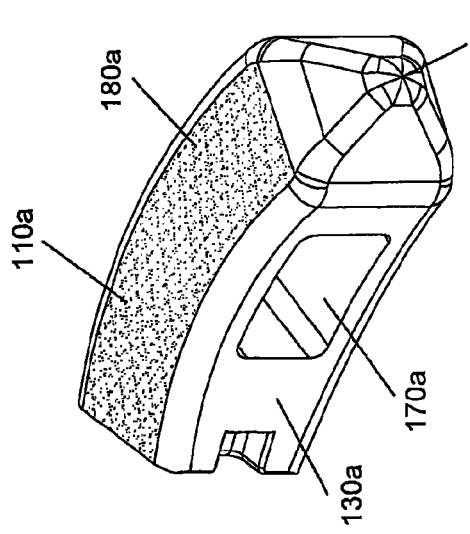
FIG. 14H shows a perspective of a curved implant, and shows the implant having a transverse aperture on a lateral side, but not the anterior portion.
Figure 14I:
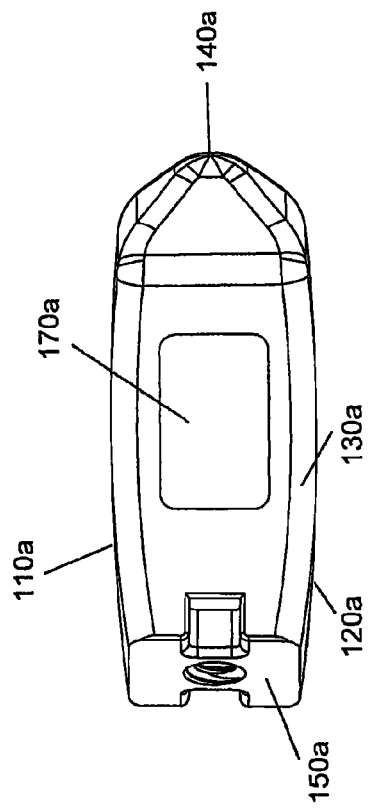
FIG. 14I shows a side perspective of a curved implant, and shows the lateral side transverse aperture.
Figure 14G:
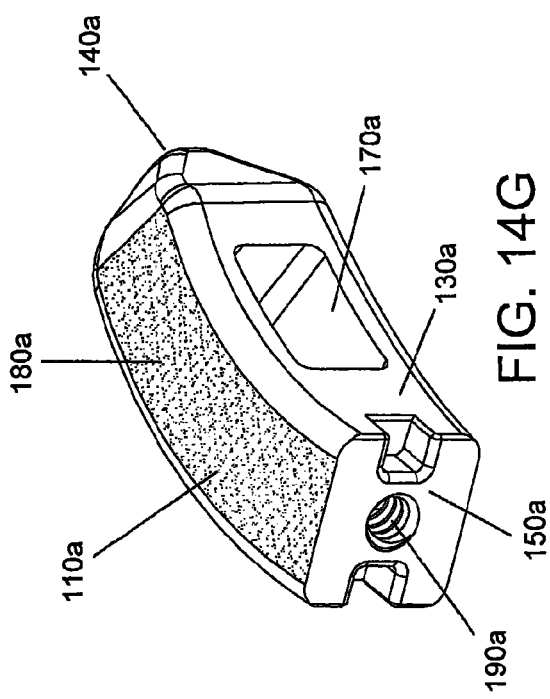
FIG. 14G shows a perspective of a curved implant, and shows the implant having a transverse aperture on a lateral side, but not the posterior portion.

In some aspects, the implant 1, 101, 101a, 201, and 301 includes a transverse aperture 70, 170, 170a, 270, and 370 on one or more of the lateral sides 30, 130, 130a, 230, and 330. FIG. 14A shows an example of a single, rectangular-shaped transverse aperture 70 on a lateral side 30 of the implant 1. FIG. 14B shows an anterior perspective of the implant 1 having a transverse aperture 70 on each lateral side 30. FIG. 14C shows a side view of the implant 1, with the rectangular transverse aperture 70 on the lateral side 30. FIG. 14D and FIG. 14E show an example of a single, circular-shaped transverse aperture 170 on each lateral side 130 of the implant 101, but not on either of the anterior 140 or posterior 150 portions. FIG. 14F shows a side view of the single, circular shaped transverse aperture 170. The configuration illustrated in FIGS. 14D-14F may also be used in a curved implant 101a, for example, as shown in FIG. 14G-14I, with the transverse aperture 170a on each of the lateral sides 130a, but not the anterior 140a or posterior 150a portions.

Figure 15A:
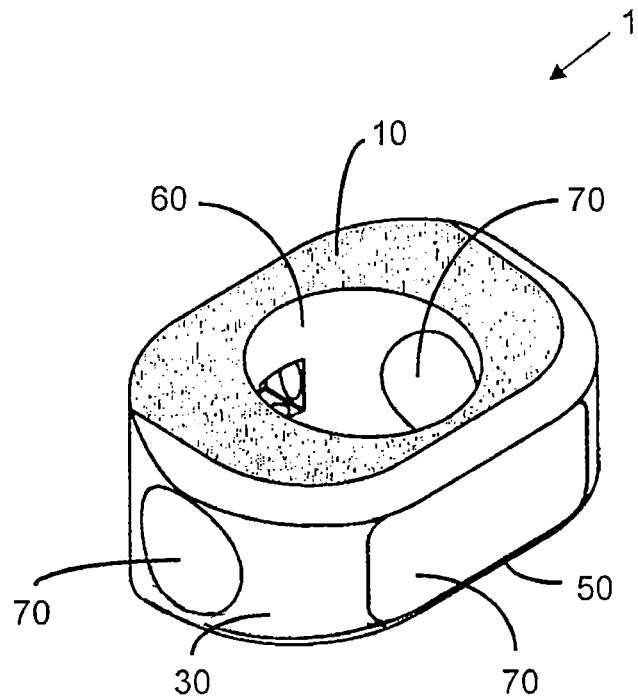
FIG. 15A shows a perspective of an oval-shaped implant having a transverse aperture on each of the lateral sides, and on the posterior portion.
Figure 15B:
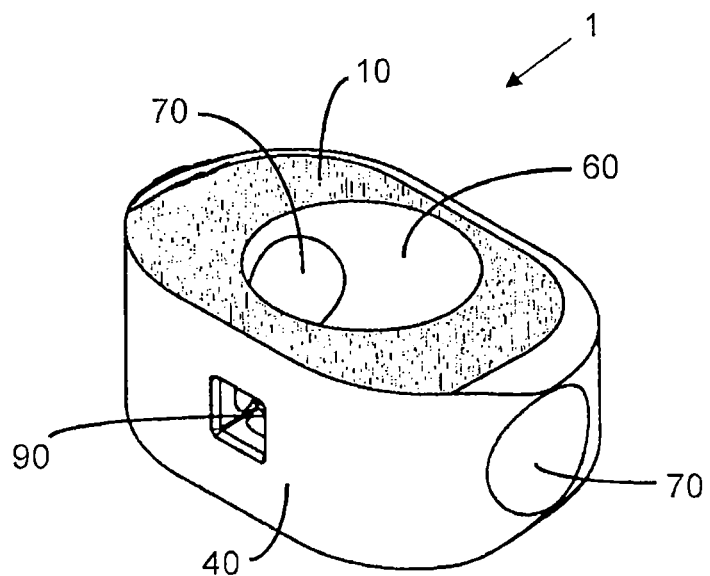
FIG. 15B shows a perspective of an oval-shaped implant having a transverse aperture on each of the lateral sides, but not on the anterior portion, though an opening for a delivery device is present on the anterior portion.

In some aspects, the implant 1, 101, 101a, 201, and 301 may have a plurality of transverse apertures 70, 170, 170a, 270, and 370, that may interconnect with the substantially hollow center and/or the single vertical aperture 60, 160, 160a, 260, and 360. The plurality of transverse apertures 70, 170, 170a, 270, and 370 may be on one or more of the lateral sides 30, 130, 130a, 230, and 330, the posterior portion 50, 150, 150a, 250, and 350, and/or the anterior portion 40, 140, 140a, 240, and 340, and/or the approximate junctions of these portions. FIG. 15A shows an example of a circular transverse aperture 70 on each lateral side 30 of the implant 1 and a rectangular transverse aperture on the posterior portion 50. The anterior portion 40 may not include a transverse aperture 70, as shown in FIG. 15B, although the anterior portion 40 may nevertheless include an opening 90 for a delivery device. An intermediate wall 72, 172, 172a, 272, and 372 may separate each of the plurality of transverse apertures 70, 170, 170a, 270, and 370. The implant 1, 101, 101a, 201, and 301 may comprise two, three, four, five, six, seven, eight, nine, ten, eleven, twelve, thirteen, fourteen, fifteen, or more transverse apertures 70, 170, 170a, 270, and 370, of any suitable shape.

FIGS. 16A-16D show an example of an implant 1 comprising a plurality of transverse apertures 70 around the perimeter, located on the posterior portion 50, the anterior portion 40, and each of the lateral sides 30. As shown, the implant 1 includes three transverse apertures 70 on each of the posterior portion 50 (FIG. 16A) and anterior portion 40 (FIG. 16B and FIG. 16C), and two transverse apertures 70 on each of the lateral sides 30 (FIG. 16A, FIG. 16B, and FIG. 16D). The number of transverse apertures 70, 170, 170a, 270, and 370 is not critical, and can vary on any number of variables, including the intended location of the implant 1, 101, 101a, 201, and 301 when inserted into the intervertebral space.

FIG. 16E shows another embodiment of an implant 101a including a plurality (two shown, without intending to be limited to two) of transverse apertures 170a on the lateral sides 130a, but not on the posterior portion 150a. FIG. 16F shows a plurality (two shown, without intending to be limited to two) of transverse apertures 170a on the lateral sides 130a, but not on the anterior portion 140a. FIG. 16G shows a plurality (two shown, without intending to be limited to two) of transverse apertures 170a on the lateral sides 130a, but not on the anterior portion 140a or on the posterior portion 150a.

Each transverse aperture 70, 170, 170a, 270, and 370 among the plurality may independently comprise any suitable shape or dimensions, which may be the same as or different from any number or all of the other members of the plurality. The space between each transverse aperture 70, 170, 170a, 270, and 370 among the plurality may be substantially the same (e.g., they are spaced substantially evenly apart), or may vary. Suitable shapes may be a substantially circular, elliptical, D-shaped, triangular, quadrilateral, rectangular, or polygonal shape. An intermediate wall 72, 172, 172a, 272, and 372 may separate each of the plurality of transverse apertures 70, 170, 170a, 270, and 370.

Figure 17:
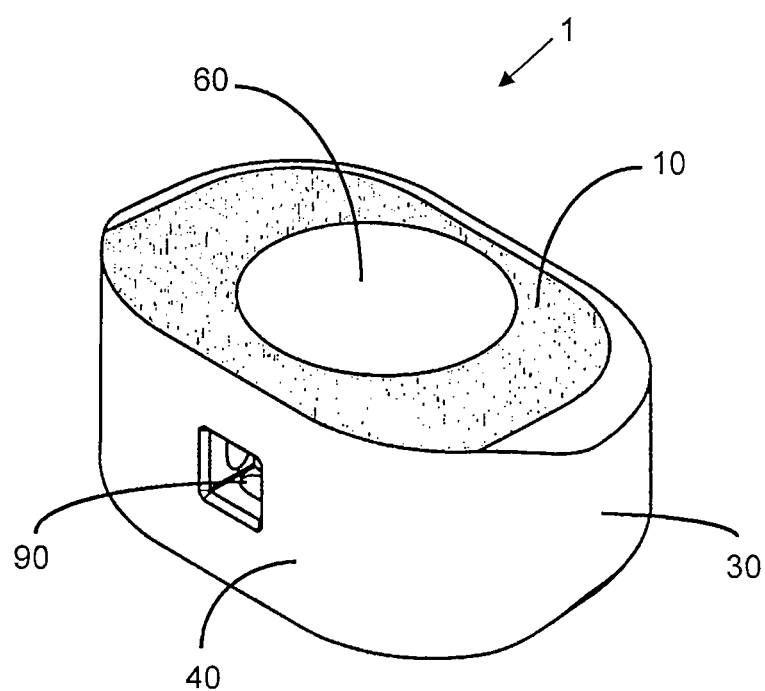
FIG. 17 shows a perspective of an oval-shaped implant having a single vertical aperture but not a transverse aperture.

The implant 1, 101, 101a, 201, and 301 need not include any transverse aperture 70, 170, 170a, 270, and 370. For example, as shown in FIG. 17, implant 1 includes no transverse aperture 70 on any of the anterior 40 or posterior portions 50, or lateral sides 30, but the implant 1 may nevertheless include an opening 90 in the anterior portion 40. The opening 90, 190, 190a, 290, and 390 is distinct from the transverse aperture 70, 170, 170a, 270, and 370, and one, the other, both, or neither may be present on an implant 1, 101, 101a, 201, and 301. The implant 1, 101, 101a, 201, and 301 may nevertheless include a single vertical aperture 60, 160, 160a, 260, and 360, as illustrated in FIG. 17.

The transverse aperture 70, 170, 170a, 270, and 370 comprises dimensions, including but not limited to a length, width, and height (or diameter) H. These dimensions may vary with the dimensions of the implant 1, 101, 101a, 201, and 301. For example, the transverse aperture height/diameter H may be about 0.5 mm to about 20 mm in height, and in some aspects may be about 1 mm to about 3 mm, about 1 mm to about 5 mm, about 1 mm to about 7 mm, about 1 mm to about 10 mm, about 1 mm to about 15 mm, about 1 mm to about 18 mm, about 2 mm to about 4 mm, about 2 mm to about 5 mm, about 2 mm to about 6 mm, about 3 mm to about 5 mm, about 3 mm to about 7 mm, about 3 mm to about 10 mm, about 3 mm to about 15 mm, about 3 mm to about 18 mm, about 4 mm to about 6 mm, about 4 mm to about 8 mm, about 5 mm to about 10 mm, about 5 mm to about 12 mm, about 5 mm to about 15 mm, about 6 mm to about 8 mm, about 6 mm to about 10 mm, about 7 mm to about 12 mm, about 7 mm to about 15 mm, about 7 mm to about 17 mm, about 8 mm to about 18 mm, about 9 mm to about 19 mm, about 10 mm to about 20 mm, about 10 mm to about 19 mm, about 10 mm to about 18 mm, about 12 mm to about 18 mm, about 12 mm to about 16 mm, or about 15 mm to about 19 mm in height. The transverse aperture height/diameter H may be about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, or more in height H.

Figure 18A:
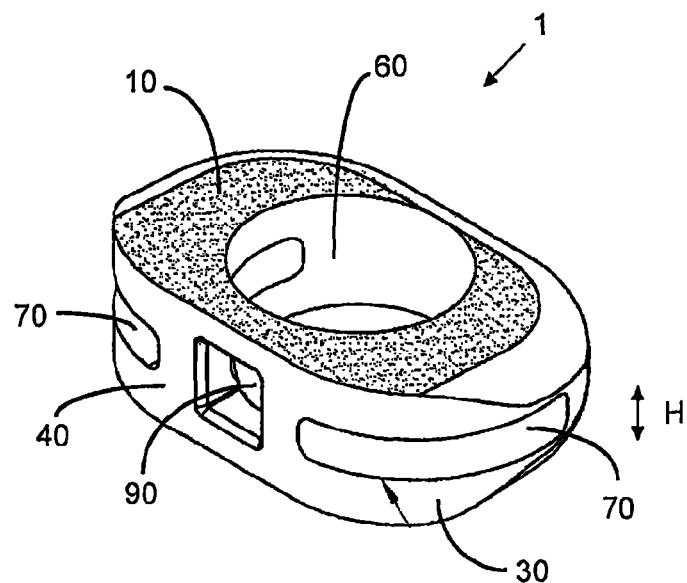
FIG. 18A shows a perspective of an oval-shaped implant having a short vertical height, with a transverse aperture on each of the lateral sides.
Figure 18B:
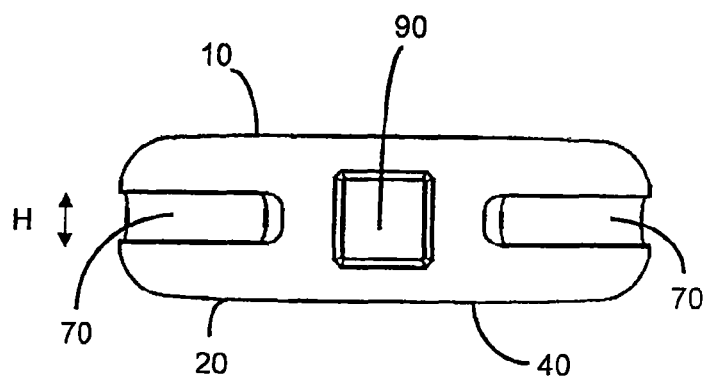
FIG. 18B shows an anterior perspective of an oval-shaped implant with a short height and a transverse aperture on each of the lateral sides.
Figure 18C:
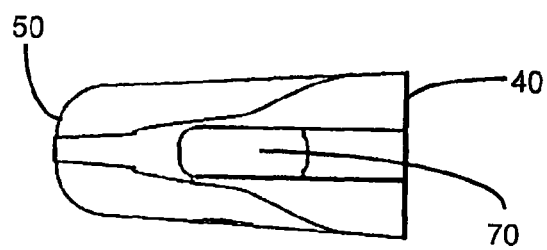
FIG. 18C shows a side perspective of an oval-shaped implant with a short height and a transverse aperture on a lateral side.
Figure 19A:
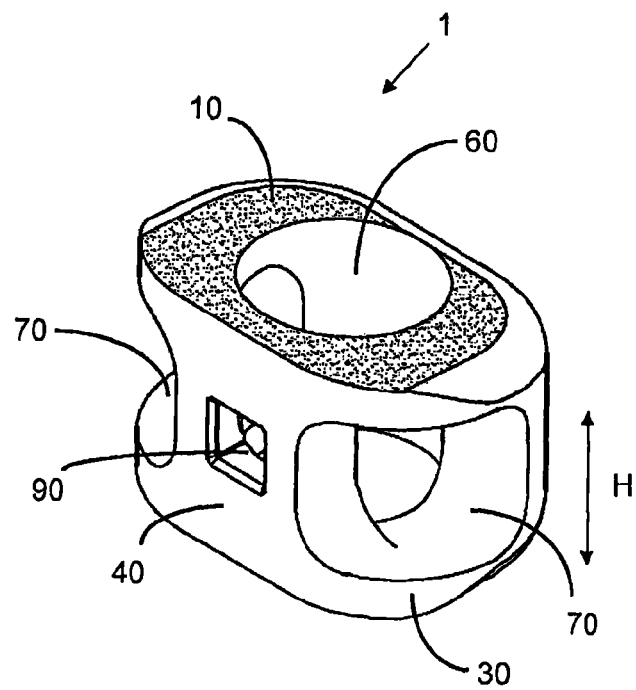
FIG. 19A shows a perspective of an oval-shaped implant having a tall vertical height, with a transverse aperture on each of the lateral sides.
Figure 19B:
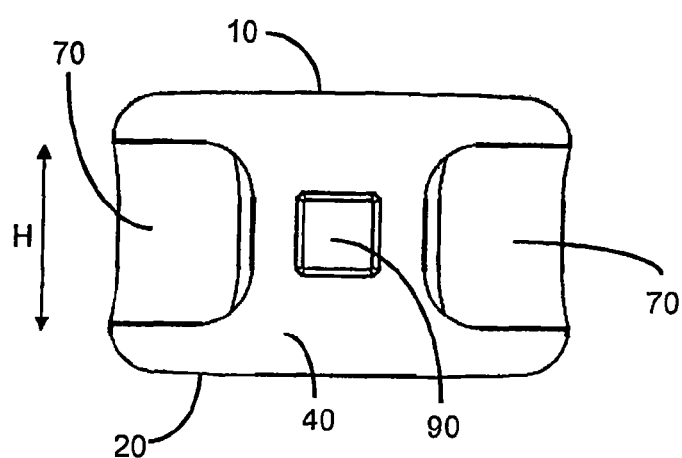
FIG. 19B shows an anterior perspective of an oval-shaped implant with a tall height and a transverse aperture on each of the lateral sides.
Figure 19C:
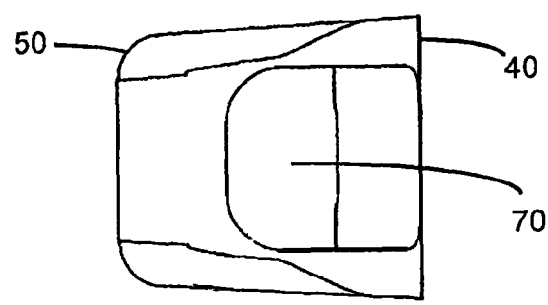
FIG. 19C shows a side perspective of an oval-shaped implant with a tall height and a transverse aperture on a lateral side.
Figure 19E:
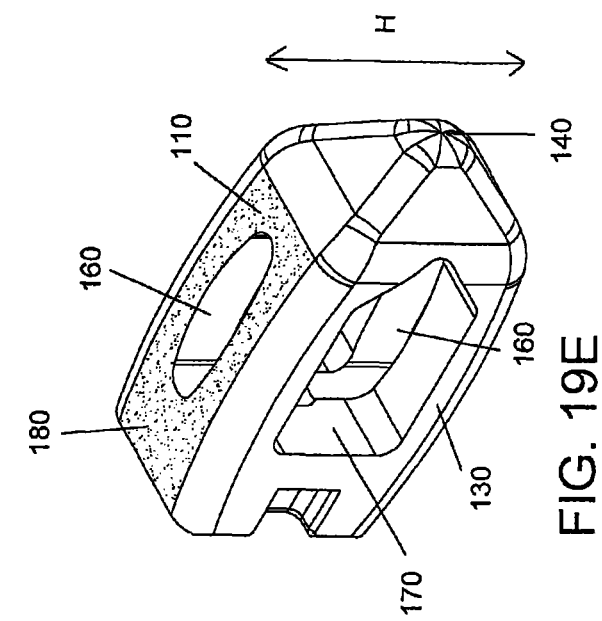
FIG. 19E shows an anterior perspective of a posterior implant with a tall height and a transverse aperture on each of the lateral sides.
Figure 19F:
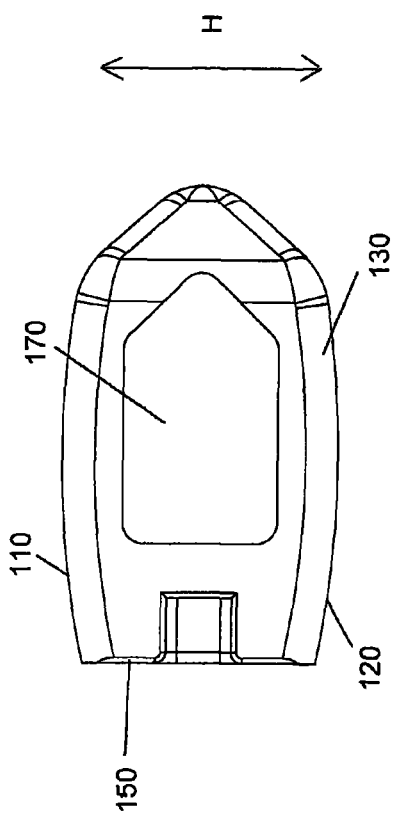
FIG. 19F shows a side perspective of a posterior implant with a tall height and a transverse aperture on a lateral side.
Figure 19D:
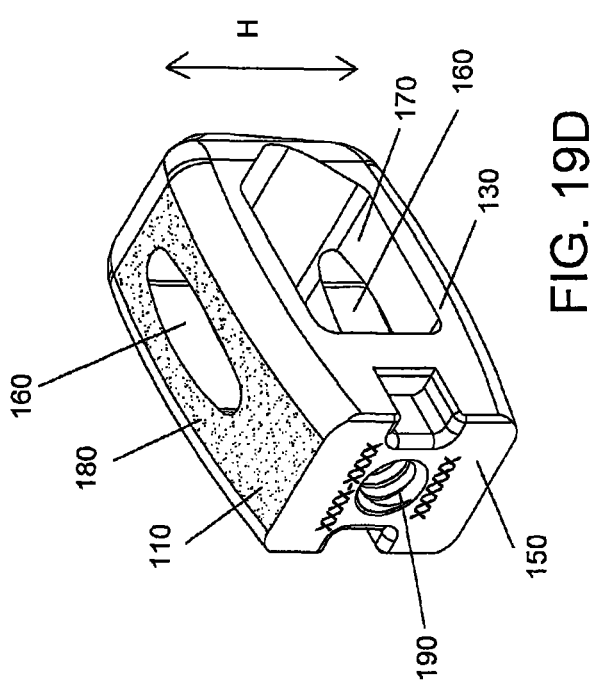
FIG. 19D shows a perspective of a posterior implant having a tall vertical height, with a transverse aperture on each of the lateral sides.

The transverse aperture height/diameter H may vary, for example, according to the height of the implant 1, 101, 101a, 201, and 301. For example, as shown in FIG. 18A-FIG. 18C, an implant 1 may have a short profile between the top portion 10 and the bottom portion 20. In such embodiments, the implant 1 may thus have a corresponding smaller transverse aperture height/diameter H relative to an implant having a larger profile between the top portion 10 and the bottom portion 20. As well, an implant 1 may have a tall profile between the top portion 10 and the bottom portion 20, as shown in FIG. 19A-FIG. 19C. An implant 101, 101a, 201, and 301 may also have a short or tall profile between the respective top portion 110, 110a, 210, and 310 and bottom portion 120, 120a, 220, and 320. FIGS. 19D-19F illustrate a posterior implant 101 with a tall profile. FIGS. 19G-19I illustrate a curved implant 101a with a tall profile.

The distance between the upper-most point of the transverse aperture 70, 170, 170a, 270, and 370 and the top surface 10, 110, 110a, 210, and 310 of may be from about 0.1 mm to about 4 mm. As well, the distance between the lower-most point of the transverse aperture 70, 170, 170a, 270, and 370 and the bottom surface 20, 120, 120a, 220, and 320 of may be from about 0.1 mm to about 3 mm. The distance between the upper-most point of the transverse aperture 70, 170, 170a, 270, and 370 and the top surface 10, 110, 110a, 210, and 310 and the distance between the lower-most point of the transverse aperture 70, 170, 170a, 270, and 370 and the bottom surface 20, 120, 120a, 220, and 320 may be the same, or may differ relative to each other. Either distance may be about 0.5 mm, about 0.7 mm, about 0.8 mm, about 1 mm, about 1.2 mm, about 1.3 mm, about 1.5 mm, about 1.7 mm, about 1.8 mm, about 2 mm, about 2.2 mm, about 2.3 mm, about 2.5 mm, about 2.7 mm, about 2.8 mm, about 3 mm, about 3.2 mm, about 3.3 mm, about 3.5 mm, about 3.7 mm, about 3.8 mm, or about 4 mm.

The transverse aperture 70, 170, 170a, 270, and 370 is preferably in communication with the hollow center of the implant 1, 101, 101a, 201, and 301. And as described above, the hollow center of the implant 1, 101, 101a, 201, and 301 is also preferably in communication with a vertical aperture 60, 160, 160a, 260, and 360. Thus, each transverse aperture 70, 170, 170a, 270, and 370 and the vertical aperture 60, 160, 160a, 260, and 360 may be in communication with each other via the hollow center, although in aspects where the implant 1, 101, 101a, 201, and 301 does not include a hollow center, each transverse aperture 70, 170, 170a, 270, and 370 may be in communication with the vertical aperture 60, 160, 160a, 260, and 360 directly. In some aspects, the implant 1, 101, 101a, 201, and 301 does not include a substantially hollow center, and in some aspects, the implant 1, 101, 101a, 201, and 301 does not include a substantially hollow center or a vertical aperture 60, 160, 160a, 260, and 360.

The transverse aperture 70, 170, 170a, 270, and 370 may comprise a notch on one or more of the lateral sides 30, 130, 130a, 230, and 330, extending from the anterior portion 40, 140, 140a, 240, and 340, to the posterior portion 50, 150, 150a, 250, and 350. For example, as shown in FIG. 20A, the implant 1 includes a notch-type transverse aperture 70 on each lateral side 30 of the implant 1, extending from the anterior portion 40 to the posterior portion 50. As shown in FIG. 20B, the implant 1 has a shape that resembles an I-beam when viewed from the anterior (or posterior) end. The notch-type transverse aperture 70, 170, 170a, 270, and 370 may comprise any suitable depth toward the center line of the implant 1, 101, 101a, 201, and 301.

Figure 20D:
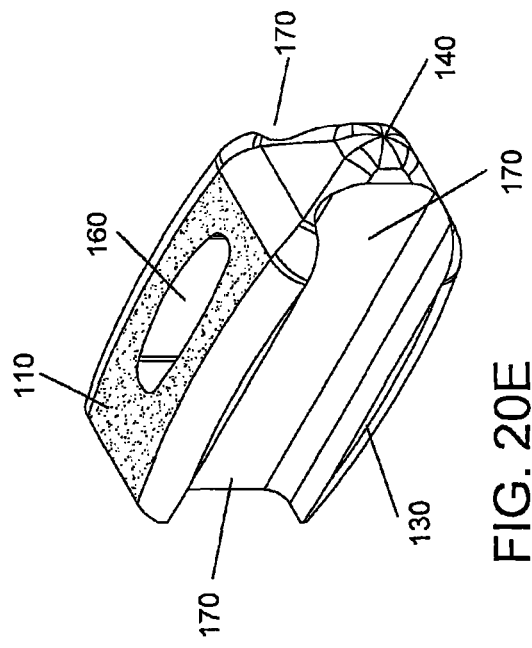
FIG. 20D shows a perspective of a posterior implant having a single vertical aperture and a transverse aperture configured as a notch into each of the lateral sides of the implant, but no transverse aperture in the posterior portion.
Figure 20E:
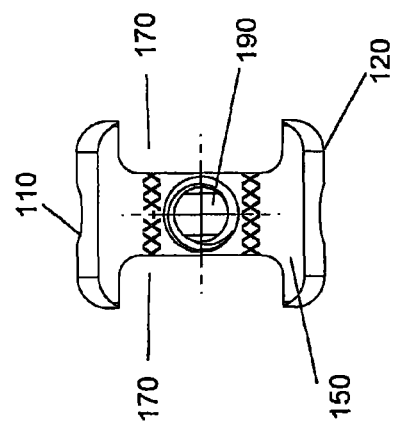
FIG. 20E shows a perspective of a posterior implant having a single vertical aperture and a transverse aperture configured as a notch into each of the lateral sides of the implant, but no transverse aperture in the anterior portion.
Figure 20F:
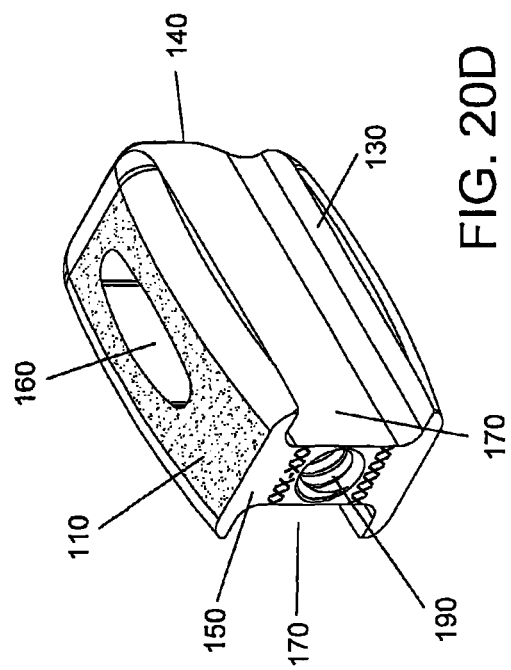
FIG. 20F shows a side perspective of a posterior implant having a transverse aperture configured as a notch into a lateral side.
Figure 20G:
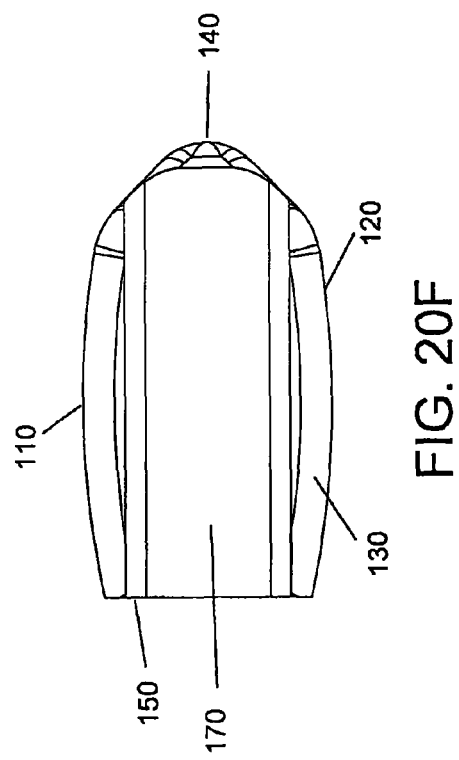
FIG. 20G shows a posterior perspective a posterior implant having a transverse aperture configured as a notch into each of the lateral sides.
Figure 20H:
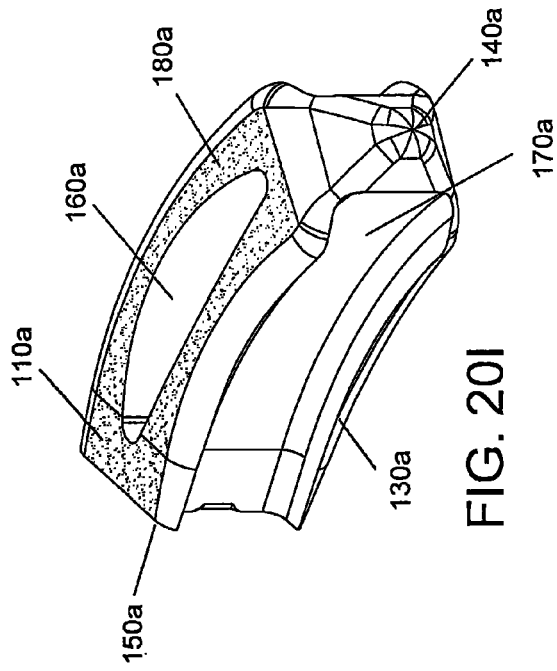
FIG. 20H shows a perspective of a curved implant having a single vertical aperture and a transverse aperture configured as a notch into each of the lateral sides of the implant, but no transverse aperture in the posterior portion.
Figure 20K:
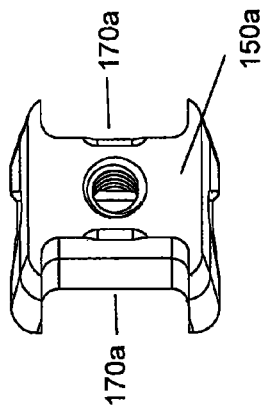
FIG. 20K shows a posterior perspective a curved implant having a transverse aperture configured as a notch into each of the lateral sides.
Figure 20I:
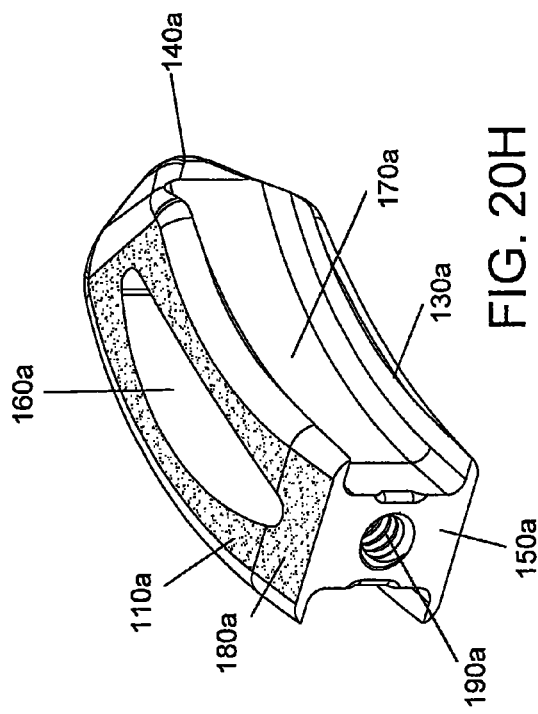
FIG. 20I shows a perspective of a curved implant having a single vertical aperture and a transverse aperture configured as a notch into each of the lateral sides of the implant, but no transverse aperture in the anterior portion.
Figure 20J:
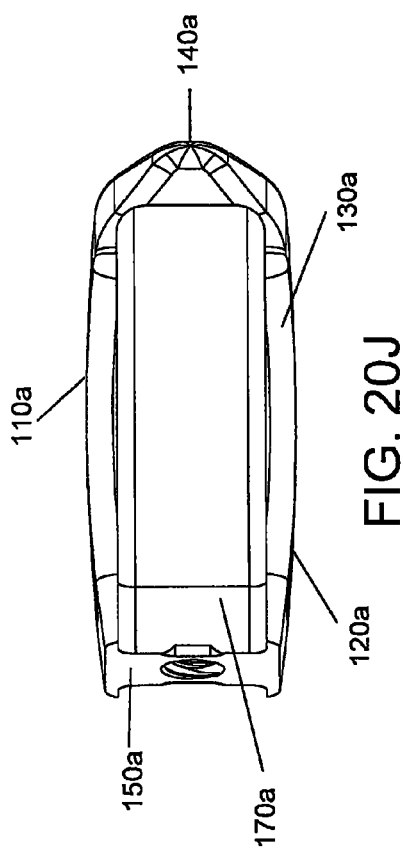
FIG. 20J shows a side perspective of a curved implant having a transverse aperture configured as a notch into a lateral side.

Although the example shown in FIG. 20A and FIG. 20B does not include a vertical aperture 60, an implant 1, 101, 101a, 201, and 301 may nevertheless include a notch-type transverse aperture 70, 170, 170a, 270, and 270 and a vertical aperture 60, 160, 160a, 260, and 360. For example, FIGS. 20D-20G show a notch-type transverse aperture 170 in the lateral sides 13 of the posterior implant 101, which also includes a vertical aperture 160. As shown, the implant 101 does not include a transverse aperture 170 in either the anterior 140 or posterior portions 150. FIGS. 20H-20K show a notch-type transverse aperture 170a in the lateral sides 130a of the curved implant 101a, which also includes a vertical aperture 160a. As shown, the implant 101a does not include a transverse aperture 170a in either the anterior 140a or posterior portions 150a. In some embodiments where the transverse aperture 70, 170, 170a, 270, and 370 comprises a notch, the implant 1, 101, 101a, 201, and 301 may not include a substantially hollow center, and the center may be substantially solid (e.g., comprised of the polymeric, composite, or metal material and provides load-bearing support).

The transverse aperture 70, 170, 170a, 270, and 370 may comprise a notch on one or more of the anterior portion 40, 140, 140a, 240, and 340 and the posterior portion 50, 150, 150a, 250, and 350, extending from one of the lateral sides 30, 130, 130a, 230, and 330 to the other. For example, as shown in FIG. 21A and FIG. 21B, the implant 1 includes a notch-type transverse aperture 70 on each of the anterior portion 40 and the posterior portion 50, extending from one lateral side 30 of the implant 1 to the other (FIG. 21D). As shown in FIG. 21C, the implant 1 has a shape that resembles an I-beam when viewed from one of the lateral sides. The notch-type transverse aperture 70, 170, 170a, 270, and 370 may comprise any suitable depth toward the center line of the implant 1, 101, 101a, 201, and 301.

Figure 21H:
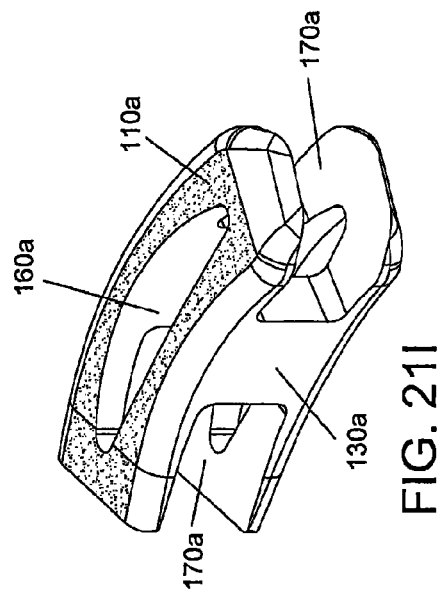
FIG. 21H shows a perspective of a curved implant having a single vertical aperture and having a transverse aperture configured as a notch into each of the anterior and posterior portions of the implant.
Figure 21I:
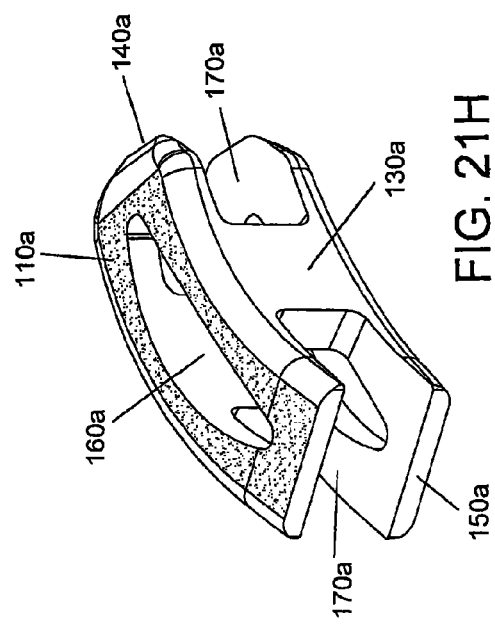
FIG. 21I shows a perspective of a curved implant having a single vertical aperture and having a transverse aperture configured as a notch into each of the anterior and posterior portions of the implant.
Figure 21J:
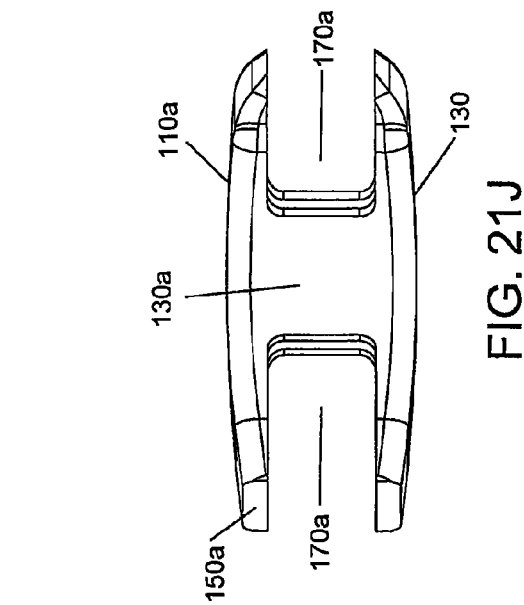
FIG. 21J shows a side perspective of a curved implant having a transverse aperture configured as a notch into each of the anterior and posterior portions of the implant.
Figure 21K:
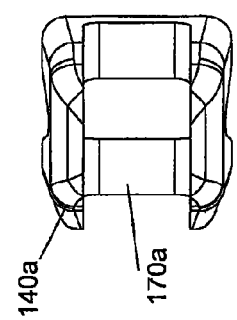
FIG. 21K shows an anterior perspective of a curved implant having a transverse aperture configured as a notch into the anterior portion of the implant.
Figure 21L:
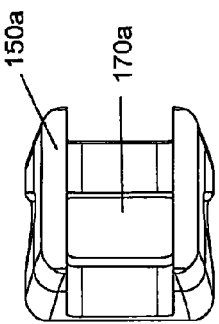
FIG. 21L shows a posterior perspective of a curved implant having a transverse aperture configured as a notch into the posterior portion of the implant.

Although the example shown in FIG. 21A and FIG. 21B does not include a vertical aperture 60, an implant 1, 101, 101a, 201, and 301 may nevertheless include a notch-type transverse aperture 70, 170, 170a, 270, and 270 and a vertical aperture 60, 160, 160a, 260, and 360. For example, FIGS. 21E-21G show a notch-type transverse aperture 170 in the anterior 140 and posterior 150 portions of a posterior implant 101, which also includes a vertical aperture 160. FIGS. 21H-21K show a notch-type transverse aperture 170a in anterior 140a and posterior 150a portions of the curved implant 101a, which also includes a vertical aperture 160a. In some embodiments where the transverse aperture 70, 170, 170a, 270, and 370 comprises a notch, the implant 1, 101, 101a, 201, and 301 may not include a substantially hollow center, and the center may be substantially solid (e.g., comprised of the polymeric, composite, or metal material and provides load-bearing support).

Figure 22A:
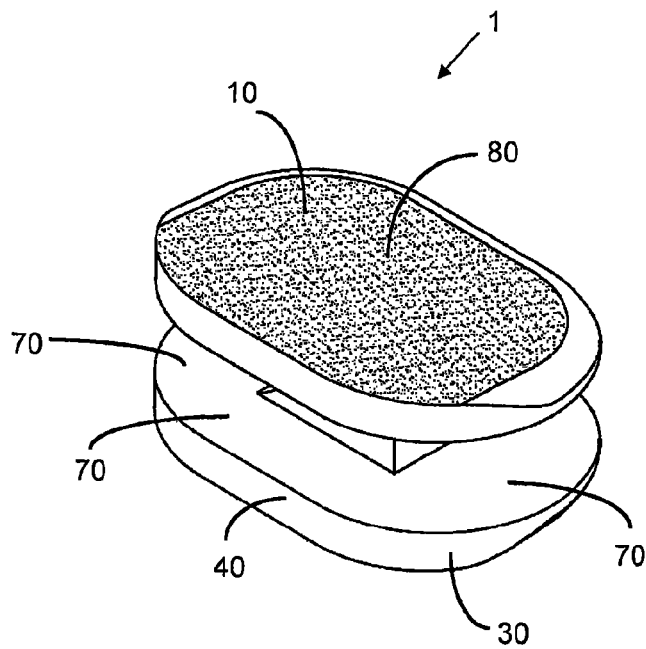
FIG. 22A shows a perspective of an oval-shaped implant having no vertical aperture and having a transverse aperture configured as a notch into each of the lateral sides as well as the anterior and posterior portions of the implant.
Figure 22B:
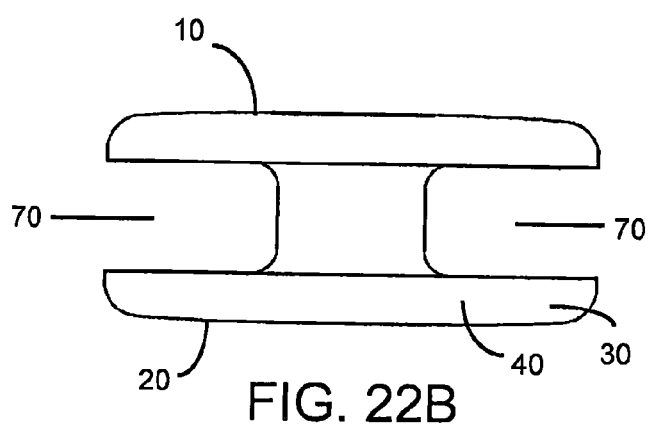
FIG. 22B shows an anterior perspective of an oval-shaped implant having no vertical aperture and having a transverse aperture configured as a notch into each of the lateral sides as well as the anterior and posterior portions of the implant.
Figure 22C:
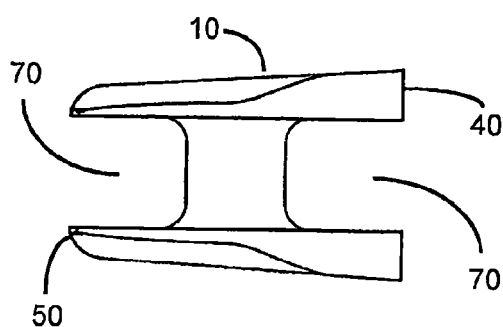
FIG. 22C shows a side perspective of an oval-shaped implant having no vertical aperture and having a transverse aperture configured as a notch into a lateral sides as well as the anterior and posterior portions of the implant.

FIG. 22A shows another example of a notch-type transverse aperture 70 on each lateral side 30 and on each of the anterior 40 and posterior portions 50 of the implant 1, effectively extending substantially around the perimeter of the implant 1. As shown in the anterior view of FIG. 22B and the lateral view of FIG. 22C, the remaining center portion of the implant, which is not substantially hollow (e.g., comprised of the polymeric, composite, or metal material and provides load-bearing support), resembles a pedestal that supports the top surface 10 and bottom surface 20 of the implant 1. The configuration of the implant 1 shown in FIGS. 22A-22C may be used with the implant 101, 101a, 201, and 301 as well (not shown). The transverse aperture 70, 170, 170a, 270, and 370 may comprise any suitable depth toward the center line of the implant 1, 101, 101a, 201, and 301. The depth of the notch may be substantially the same among the lateral sides 30, 130, 130a, 230, and 330, and anterior 40, 140, 140a, 240, and 340, and posterior portions 50, 150, 150a, 250, and 350. The depth of the notch may vary, and may vary independently among the lateral sides 30, 130, 130a, 230, and 330, and anterior 40, 140, 140a, 240, and 340, and posterior portions 50, 150, 150a, 250, and 350. Although the example shown in FIGS. 22A-22C does not include a vertical aperture 60, an implant 1, 101, 101a, 201, and 301 may nevertheless include a notch-type transverse aperture 70, 170, 170a, 270, and 270 and a vertical aperture 60, 160, 160a, 260, and 360 (not shown), for example, by having the notch extend less deeply, thereby allowing more area for the vertical aperture 60, 160, 160a, 260, and 360.

Whether configured as a notch or a hole, the transverse aperture 70, 170, 170a, 270, and 370 may be filled with a bone graft material, including any described or exemplified herein. As well, the transverse aperture 70, 170, 170a, 270, and 370 may be used to facilitate positioning of the implant 1, 101, 101a, 201, and 301 during the implantation procedure. When used to facilitate positioning of the implant 1, 101, 101a, 201, and 301, the transverse aperture 70, 170, 170a, 270, and 370 may be filled with a bone graft material after the practitioner has established the final position of the implant 1, 101, 101a, 201, and 301.

Figure 23A:
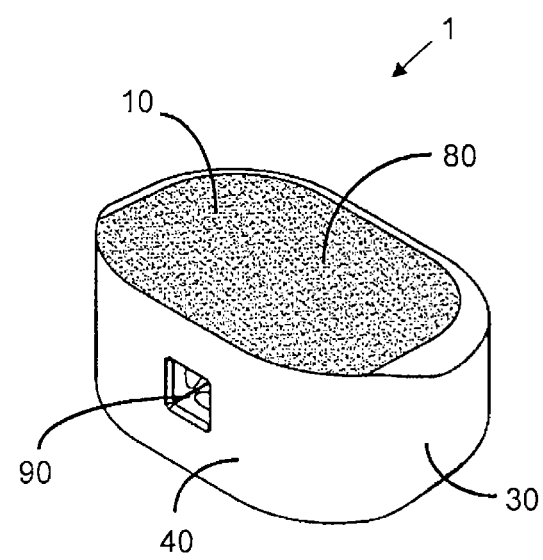
FIG. 23A shows a perspective of an oval-shaped implant having no vertical aperture and no transverse aperture.
Figure 23B:
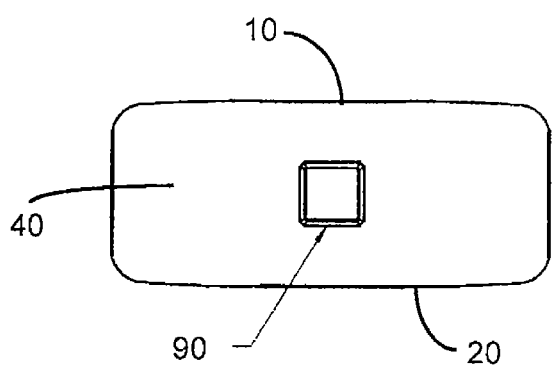
FIG. 23B shows an anterior perspective of an oval-shaped implant having no vertical aperture and no transverse aperture.
Figure 23C:
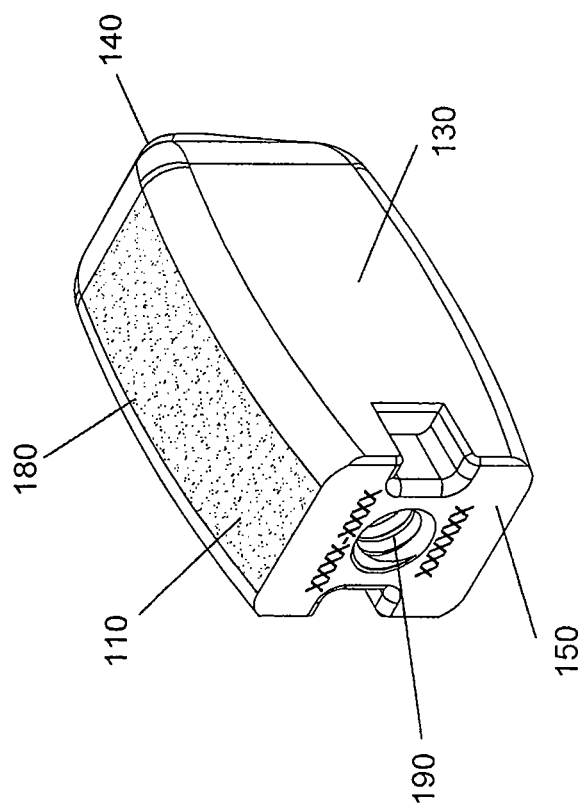
FIG. 23C shows a perspective of a posterior implant having no vertical aperture and no transverse aperture.
Figure 23D:
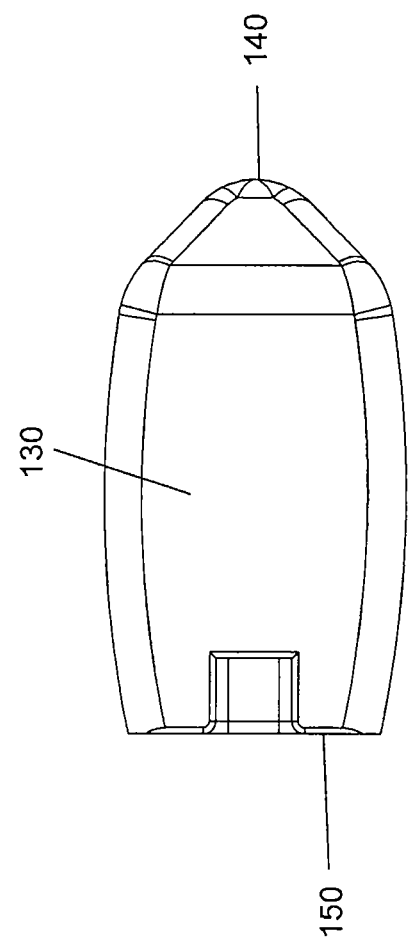
FIG. 23D shows a side perspective of a posterior implant having no vertical aperture and no transverse aperture.
Figure 23E:
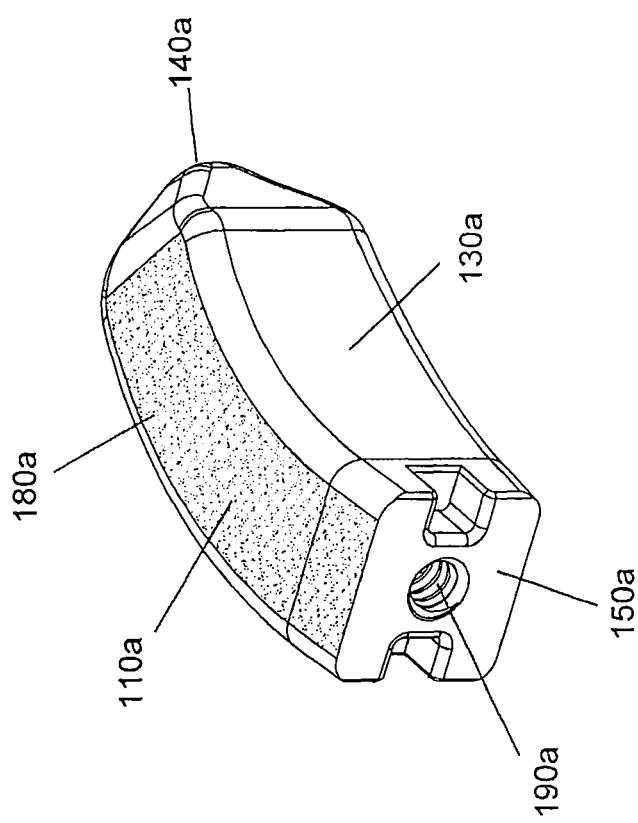
FIG. 23E shows a perspective of a curved implant having no vertical aperture and no transverse aperture.
Figure 23F:
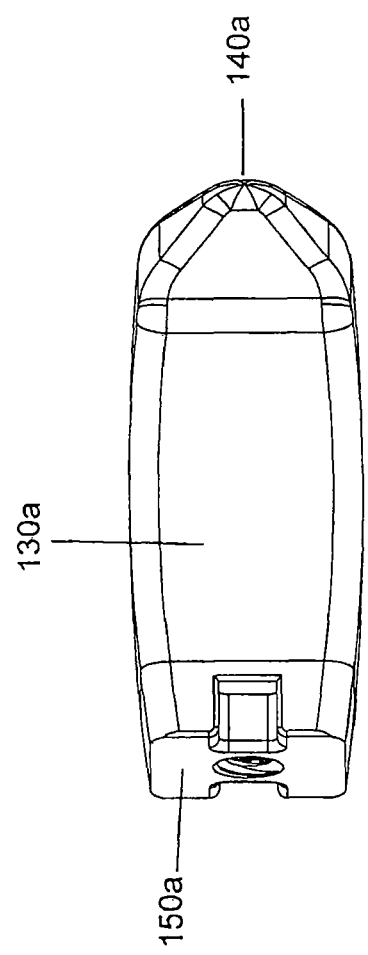
FIG. 23F shows a side perspective of a curved implant having no vertical aperture and no transverse aperture.

In some aspects, the implant 1, 101, 101a, 201, and 301 does not include a vertical aperture 60, 160, 160a, 260, and 360 or a transverse aperture 70, 170, 170a, 270, and 370, for example, as shown in FIGS. 23A-23F. In FIG. 23A, the roughened surface topography 80 spans the entire integration surface of the top surface 10 of the implant 1, in FIG. 23D, the roughened surface topography 180 spans the entire integration surface of the top surface 110 of the implant 101, and in FIG. 23F, the roughened surface topography 180a spans the entire integration surface of the top surface 110a of the implant 101a. The implant 1, 101, 101a, 201, and 301, though lacking a vertical aperture 60, 160, 160a, 260, and 360 and a transverse aperture 70, 170, 170a, 270a and 370, may nevertheless include an opening 90, 190, 190a, 290, and 390 in the anterior portion 40 as shown in FIG. 23A and FIG. 23B, or in the posterior portion 150 and 150a as shown in FIG. 23D and FIG. 23F, and this opening 90, 190, 190a, 290, and 390 may be used for a connection with a delivery device during implantation.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1, 101, 101a, 201, and 301 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant is to be seated near the center of the vertebral endplate or the implant is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101a, 201, and 301 include smooth, rounded, and highly radiused posterior portions and lateral sides which may minimize extraneous bone removal for endplate preparation and reduce localized stress concentrations. Thus, interbody surgical implant 1, 101, 101a, 201, and 301 and methods of using it are particularly useful in preserving the natural arch of the vertebral endplate and minimizing the chance of implant subsidence.

Because the endplates are spared during the process of inserting the spinal implant 1, 101, 101a, 201, and 301, hoop stress of the inferior and superior endplates is maintained. Spared endplates allow the transfer of axial stress to the apophasis. Endplate flexion allows the bone graft placed in the interior of the spinal implant 1 to accept and share stress transmitted from the endplates. In addition, spared endplates minimize the concern that BMP might erode the cancellous bone.

Certain embodiments of the interbody spinal implant 1, 101, 101a, 201, and 301 may maintain a position between the vertebral endplates due, at least in part, to resultant annular tension attributable to press-fit surgical implantation and, post-operatively, improved osteointegration at the top surface 10, 110, 110a, 210, and 310; the bottom surface 20, 120, 120a, 220, and 320; or both surfaces.

Surgical implants and methods tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implant 1, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101a, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101a, 201, and 301 may be used as the final distractor and thus maintain the relative position of the vertebrae without the need for secondary instrumentation.

Certain embodiments collectively comprise a family of implants, each having a common design philosophy. These implants and the associated surgical technique have been designed to address at least the ten, separate challenges associated with the current generation of traditional anterior spinal fusion devices listed above in the Background section of this document.

Embodiments of the invention allow end-plate preparation with custom-designed rasps. These rasps preferably have a geometry matched with the geometry of the implant. The rasps conveniently remove cartilage from the endplates and remove minimal bone, only in the postero-lateral regions of the vertebral end-plates. It has been reported in the literature that the end-plate is the strongest in postero-lateral regions.

After desired annulotomy and discectomy, embodiments of the invention first adequately distract the disc space by inserting (through impaction) and removing sequentially larger sizes of very smooth distractors, which have been size matched with the size of the available implant 1, 101, 101a, 201, and 301. Once adequate distraction is achieved, the surgeon prepares the end-plate with a rasp. There is no secondary instrumentation required to keep the disc space distracted while the implant 1, 101, 101a, 201, and 301 is inserted, as the implant 1, 101, 101a, 201, and 301 has sufficient mechanical strength that it is impacted into the disc space. In fact, the height of the implant 1, 101, 101a, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101a, 201, and 301 has adequate strength to allow impact. The sides of the implant 1, 101, 101a, 201, and 301 have smooth surfaces, included rounded or tapered edges to allow for easy implantation and, specifically, to prevent binding of the implant 1, 101, 101a, 201, and 301 to soft tissues during implantation.

The invention encompasses a number of different implant 1, 101, 101a, 201, and 301 configurations, including a one-piece, titanium-only implant and a composite implant formed of top and bottom plates (components) made out of titanium, including an implant body formed of a polymeric material including one or more integration plates formed of a metal such as titanium. The surfaces exposed to the vertebral body are dual acid etched to allow for bony in-growth over time, and to provide resistance against expulsion. The top and bottom titanium plates are assembled together with the implant body that is injection molded with PEEK. The net result is a composite implant that has engineered stiffness for its clinical application.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101a, 201, and 301 designed according to certain embodiments allows the vertebral end-plate to deflect and allows healing of the bone graft into fusion.

The roughened topography 80, 180, 180a, 280, and 380 whether directly on the top/bottom surface of the implant 1, 101, 101a, 201, and 301 or the integration plate 82, 182, 182a, 282, and 382 reacts with contacting bone to promote biologic activities that facilitate fusion of bone to the implant 1, 101, 101a, 201, and 301.

The implant 1, 101, 101a, 201, and 301 may comprise a lordotic angle L, e.g., may be wedge-shaped to facilitate sagittal alignment. Thus, for example, the anterior portion 40, 140, 140a, 240, and 340 of the implant 1, 101, 101a, 201, and 301 may comprise a height that is larger than the height of the posterior portion 50, 150, 150a, 250, and 350. The lordotic angle L may be established by the implant 1, 101, 101a, 201, and 301 itself, or may be established by the integration plate 82, 182, 182a, 282, and 382 when combined with the implant 1, 101, 101a, 201, and 301.

The lordotic angle L of the implant 1 preferably closely approximates, or otherwise is substantially the same as, the angle of lordosis of the spine of the patient where the implant 1, 101, 101a, 201, and 301 will be implanted. In some aspects, the integration plate 82, 182, 182a, 282, and 382 increases the lordotic angle L by about 3% to about 5%, measured according to the angle of lordosis of a particular patient's spine.

The implant 1, 101, 101a, 201, and 301 may have a lordotic angle L about 3%, about 3.3%, about 3.5%, about 3.7%, about 4%, about 4.3%, about 4.5%, about 4.7%, or about 5% greater than the patient's angle of lordosis, though percentages greater than 5% or lesser 3% are possible. The increase of about 3% to about 5% preferably results from the combination of the protruding height of the integration plate 82, 182, 182a, 282, and 382 on the top portion 10, 110, 110a, 210, and 310 and bottom portion 20, 120, 120a, 220, and 320 of the implant 1, 101, 101a, 201, and 301.

The expulsion-resistant edge 8, 108, 108a, 208, and 308 may comprise an anti-expulsion edge angle E. The anti-expulsion edge angle E may be from about 80 degrees to about 100 degrees. In preferred aspects, the anti-expulsion edge angle E may be measured by taking into account the lordosis angle L of the implant 1, 101, 101a, 201, and 301. In highly preferred aspects, the anti-expulsion edge angle E is measured by subtracting half of the lordotic angle L from 90 degrees. For example, where the lordosis angle L of the implant 1, 101, 101a, 201, and 301 is 12 degrees, the anti-expulsion edge angle E is 84 degrees (90−(12×0.5)). The anti-expulsion edge angle E may be about 80 degrees, about 81 degrees, about 82 degrees, about 83 degrees, about 84 degrees, about 85 degrees, about 86 degrees, about 86.5 degrees, about 87 degrees, about 88 degrees, or about 89 degrees.

The top and bottom surfaces of the implant may be made out of titanium and are dual acid etched. The dual acid etching process creates a highly roughened texture on these surfaces, which generates tremendous resistance to expulsion. The width of these dual acid etched surfaces is very broad and creates a large area of contact with the vertebral end-plates, further increasing the resistance to expulsion.

The implant 1, 101, 101a, 201, and 301 according to certain embodiments of the invention has a large foot-print, and offers several sizes. Because there is no secondary instrument required to maintain distraction during implantation, all the medial-lateral (ML) exposure is available as implantable ML width of the implant 1, 101, 101a, 201, and 301. This feature allows the implant 1, 101, 101a, 201, and 301 to contact the vertebral end-plates at the peripheral apophyseal rim, where the end-plates are the strongest and least likely to subside.

Further, there are no teeth on the top and bottom surfaces (teeth can create stress risers in the end-plate, encouraging subsidence). Except for certain faces, all the implant surfaces have heavily rounded edges, creating a low stress contact with the end-plates. The wide rim of the top and bottom surfaces, in contact with the end-plates, creates a low-stress contact due to the large surface area. Finally, the implant construct has an engineered stiffness to minimize the stiffness mismatch with the vertebral body which it contacts.

Even the titanium-only embodiment of the invention has been designed with large windows to allow for radiographic evaluation of fusion, both through AP and lateral X-rays. A composite implant minimizes the volume of titanium, and localizes it to the top and bottom surfaces. The rest of the implant is made of PEEK which is radiolucent and allows for free radiographic visualization.

Although illustrated and described above with reference to certain specific embodiments and examples, the invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed:

1. An interbody spinal implant, comprising:
    a body generally oval-shaped in transverse cross-section having a top surface, a bottom surface, opposing lateral sides, opposing anterior and posterior portions, and a substantially hollow center, the opposing lateral sides defining a length of the body and the opposing anterior and posterior portions defining a width of the body;
    at least one transverse aperture located on one or more of the posterior portion, the anterior portion, and at least one of the opposing lateral sides, positioned substantially centrally between the top surface and the bottom surface, extending through the width or the length of the body, and in communication with the substantially hollow center;
    a single vertical aperture extending from the top surface to the bottom surface and defining a transverse rim with a varying thickness on the top surface and on the bottom surface having an anterior section, a posterior section, opposing lateral sections, and a maximum width at its center;
    generally rounded, blunt, and radiused intersections defined along the entire lengths between the top and bottom surfaces and the lateral sides, and the top and bottom surfaces and the posterior portion;
    a roughened surface topography, without teeth, adapted to grip bone and inhibit migration of the implant on at least a portion of the top surface, the bottom surface, or both the top and bottom surfaces that is not generally rounded and blunt; and
    at least one sharp edge between the top and bottom surfaces and the anterior portion to resist pullout.

2. The interbody spinal implant of claim 1, wherein the implant comprises at least one transverse aperture on the posterior portion, and at least one transverse aperture on the anterior portion.

3. The interbody spinal implant of claim 2, wherein the at least one transverse aperture on the posterior portion and the at least one transverse aperture on the anterior portion extend into the substantially hollow center.

4. The interbody spinal implant of claim 3, wherein the at least one transverse aperture on the posterior portion and the at least one transverse aperture on the anterior portion each comprise a notch.

5. The interbody spinal implant of claim 1, wherein the implant comprises at least one transverse aperture on each of the opposing lateral sides, wherein the implant does not have a transverse aperture on the anterior portion, and wherein the anterior portion has an opening for engaging a delivery device.

6. The interbody spinal implant of claim 5, wherein the implant comprises at least one transverse aperture on the posterior portion.

7. The interbody spinal implant of claim 5, wherein the at least one transverse aperture on each of the opposing lateral sides extends into the substantially hollow center.

8. The interbody spinal implant of claim 5, wherein the at least one transverse aperture on each of the opposing lateral sides comprises a notch.

9. The interbody spinal implant of claim 1, wherein the implant comprises at least one transverse aperture on the posterior portion, on the anterior portion, and on each of the opposing lateral sides.

10. The interbody spinal implant of claim 9, wherein the at least one transverse aperture on the posterior portion, on the anterior portion, and on each of the opposing lateral sides extends into the substantially hollow center.

11. The interbody spinal implant of claim 9, wherein the at least one transverse aperture on the posterior portion, on the anterior portion, and on each of the opposing lateral sides comprises a notch.

12. The interbody spinal implant of claim 9, wherein the implant comprises a plurality of transverse apertures on the posterior portion, on the anterior portion, and on each of the opposing lateral sides, and wherein each of the plurality of transverse apertures extends into the substantially hollow center.

13. The interbody spinal implant of claim 1, wherein the implant comprises at least one transverse aperture on each of the opposing lateral sides, wherein the implant does not have a transverse aperture on the posterior portion, and wherein the posterior portion has an opening for engaging a delivery device.

14. The interbody spinal implant of claim 13, wherein the at least one transverse aperture on each of the opposing lateral sides extends into the substantially hollow center.

15. The interbody spinal implant of claim 13 wherein the at least one transverse aperture on each of the opposing lateral sides comprises a notch.

16. The interbody spinal implant of claim 1, further comprising bone graft material disposed in the at least one transverse aperture, optionally also disposed in the substantially hollow center of the body, and optionally also disposed in the vertical aperture.

17. The interbody spinal implant of claim 16, wherein the bone graft material is cancellous autograft bone, allograft bone, demineralized bone matrix (DBM), porous synthetic bone graft substitute, bone morphogenic protein (BMP), or a combination thereof.

18. The interbody spinal implant of claim 1, further comprising a lordotic angle adapted to facilitate alignment of the spine.

19. The interbody spinal implant of claim 1, wherein the at least one transverse aperture is in the form of a notch on one or more of the posterior portion, the anterior portion, and at least one of the opposing lateral sides, to define a pedestal that supports the top surface and the bottom surface.

20. The interbody spinal implant of claim 1, wherein the at least one transverse aperture is circular in shape.

21. The interbody spinal implant of claim 1, wherein the at least one transverse aperture is quadrilateral in shape.

22. The interbody spinal implant of claim 1 further comprising bone graft material disposed in the at least one transverse aperture, in the substantially hollow center of the body, and in the vertical aperture.

23. An interbody spinal implant, comprising:
a body generally rectangular-shaped in transverse cross-section having a top surface, a bottom surface, opposing lateral sides, opposing anterior and posterior portions, and a substantially hollow center, the opposing lateral sides defining a width of the body and the opposing anterior and posterior portions defining a length of the body;
at least one transverse aperture located on one or more of the posterior portion, the anterior portion, and at least one of the opposing lateral sides and positioned between the top surface and the bottom surface, extending through the width or the length of the body, and in communication with the substantially hollow center;
a single vertical aperture extending from the top surface to the bottom surface and defining a transverse rim with a varying thickness on the top surface and on the bottom surface having an anterior section, a posterior section, opposing lateral sections, a maximum width at its center, the transverse rim having a generally rounded, blunt, and radiused portion defined along top and the lateral sides along the entire lengths between the top and bottom surfaces of each lateral side and the top and bottom surfaces and the anterior portion, wherein the entire portion of the transverse rim that is not blunt and radiused has a roughened surface topography, without teeth, adapted to grip bone and inhibit migration of the implant; and
at least one sharp edge between the to and bottom surfaces and the posterior portion to resist pullout.

24. An interbody spinal implant, comprising:
a body generally curve-shaped in transverse cross section having a top surface, a bottom surface, opposing lateral sides, opposing anterior and posterior portions, and a substantially hollow center, the opposing lateral sides defining a width of the body and the opposing anterior and posterior portions defining a length of the body;
at least one transverse aperture located on one or more of the posterior portion, the anterior portion, and at least one of the opposing lateral sides, positioned between the top surface and the bottom surface, and extending through the width or the length of the body, and in communication with the substantially hollow center;
a single vertical aperture extending from the top surface to the bottom surface and defining a transverse rim with a varying thickness on the top surface and on the bottom surface having an anterior section, a posterior section, opposing lateral sections, and a maximum width at its center, the transverse rim having a generally rounded, blunt, and radiused intersections defined along the top and bottom surfaces and each lateral side and the top and bottom surfaces and the anterior portion, wherein the entire portion of the transverse rim that is not blunt and radiused has a roughened surface topography adapted to grip bone and inhibit migration of the implant; and
at least one sharp edge between the top and bottom surfaces and the anterior portion or the posterior portion to resist pullout.

\* \* \* \* \*